US008764652B2

(12) United States Patent
Lee et al.

(10) Patent No.: US 8,764,652 B2
(45) Date of Patent: Jul. 1, 2014

(54) METHOD AND SYSTEM FOR MEASURING AND RANKING AN "ENGAGEMENT" RESPONSE TO AUDIOVISUAL OR INTERACTIVE MEDIA, PRODUCTS, OR ACTIVITIES USING PHYSIOLOGICAL SIGNALS

(75) Inventors: Hans C. Lee, Carmel, CA (US); Timmie T. Hong, San Diego, CA (US); William H. Williams, Hilo, HI (US); Michael R. Fettiplace, Madison, WI (US); Michael J. Lee, Carmel, CA (US)

(73) Assignee: The Nielson Company (US), LLC., Schaumburg, IL (US)

( * ) Notice: Subject to any disclaimer, the term of this patent is extended or adjusted under 35 U.S.C. 154(b) by 1042 days.

(21) Appl. No.: 11/845,993

(22) Filed: Aug. 28, 2007

(65) Prior Publication Data

US 2008/0221400 A1      Sep. 11, 2008

Related U.S. Application Data

(60) Provisional application No. 60/905,447, filed on Mar. 8, 2007.

(51) Int. Cl.
*A61B 5/00*        (2006.01)
*G06F 19/00*       (2011.01)
(52) U.S. Cl.
CPC ..................................... *G06F 19/34* (2013.01)
USPC ........................................................ 600/301
(58) Field of Classification Search
None
See application file for complete search history.

(56) References Cited

U.S. PATENT DOCUMENTS

| | | | |
|---|---|---|---|
| 4,695,879 | A | 9/1987 | Weinblatt |
| 4,755,045 | A | 7/1988 | Borah et al. |
| 4,846,190 | A | 7/1989 | John |
| 4,931,934 | A | 6/1990 | Snyder |
| 4,974,602 | A | 12/1990 | Abraham-Fuchs et al. |
| 5,024,235 | A | 6/1991 | Ayers |
| 5,243,517 | A | 9/1993 | Schmidt et al. |
| 5,406,957 | A | 4/1995 | Tansey |
| 5,447,166 | A * | 9/1995 | Gevins ........................ 600/544 |
| 5,450,855 | A | 9/1995 | Rosenfeld |

(Continued)

FOREIGN PATENT DOCUMENTS

| | | |
|---|---|---|
| EP | 1052582 | 11/2000 |
| EP | 1389012 | 2/2004 |

(Continued)

OTHER PUBLICATIONS

Form PCT/ISA/220, PCT/US07/15019, "PCT Notification of Transmittal of the International Search Report and the Written Opinion of the International Searching Authority, or the Declaration," 1 pg.

(Continued)

*Primary Examiner* — Gary Jackson
*Assistant Examiner* — Bobby Soriano
(74) *Attorney, Agent, or Firm* — Hanley, Flight & Zimmerman LLC

(57) ABSTRACT

A system and method for calculating an engagement value by quantifying an amount that a user is acting without thinking considering brainwaves and a heart rate can be used to compare media based on an individual or a group of individuals. Events of the media can be contrasted and compared by the engagement value as well. Statistical measurements may be taken to improve media.

36 Claims, 11 Drawing Sheets

(56) References Cited

U.S. PATENT DOCUMENTS

| | | |
|---|---|---|
| 5,513,649 A | 5/1996 | Gevins et al. |
| 5,579,774 A | 12/1996 | Miller et al. |
| 5,601,090 A | 2/1997 | Musha |
| 5,649,061 A | 7/1997 | Smyth |
| 5,676,138 A | 10/1997 | Zawilinski |
| 5,692,906 A | 12/1997 | Corder |
| 5,724,987 A | 3/1998 | Gevins et al. |
| 5,740,812 A | 4/1998 | Cowan |
| 5,774,591 A | 6/1998 | Black et al. |
| 5,983,129 A | 11/1999 | Cowan et al. |
| 5,983,214 A | 11/1999 | Lang et al. |
| 6,001,065 A | 12/1999 | DeVito |
| 6,099,319 A | 8/2000 | Zaltman et al. |
| 6,254,536 B1 | 7/2001 | DeVito |
| 6,259,889 B1* | 7/2001 | LaDue ............... 434/308 |
| 6,292,688 B1 | 9/2001 | Patton |
| 6,309,342 B1* | 10/2001 | Blazey et al. ............ 600/26 |
| 6,322,368 B1 | 11/2001 | Young et al. |
| 6,349,231 B1* | 2/2002 | Musha ................ 600/544 |
| 6,425,764 B1* | 7/2002 | Lamson ............... 434/236 |
| 6,434,419 B1 | 8/2002 | Gevins et al. |
| 6,481,013 B1 | 11/2002 | Dinwiddie et al. |
| 6,585,521 B1 | 7/2003 | Obrador |
| 6,606,102 B1 | 8/2003 | Odom |
| 6,609,024 B1 | 8/2003 | Ryu et al. |
| 6,623,428 B2 | 9/2003 | Miller et al. |
| 6,626,676 B2 | 9/2003 | Freer |
| 6,648,822 B2 | 11/2003 | Hamamoto et al. |
| 6,652,283 B1 | 11/2003 | Van Schaack et al. |
| 6,656,116 B2 | 12/2003 | Kim et al. |
| 6,678,866 B1 | 1/2004 | Sugimoto et al. |
| 6,699,188 B2* | 3/2004 | Wessel ............... 600/300 |
| 6,792,304 B1 | 9/2004 | Silberstein |
| 6,839,682 B1 | 1/2005 | Blume |
| 6,978,115 B2 | 12/2005 | Whitehurst et al. |
| 7,035,685 B2 | 4/2006 | Ryu et al. |
| 7,050,753 B2 | 5/2006 | Knutson |
| 7,113,916 B1 | 9/2006 | Hill |
| 7,127,283 B2 | 10/2006 | Kageyama |
| 7,194,186 B1 | 3/2007 | Strub et al. |
| D565,735 S | 4/2008 | Washbon |
| 7,383,728 B2 | 6/2008 | Noble et al. |
| 7,627,880 B2 | 12/2009 | Itakura |
| 7,689,272 B2* | 3/2010 | Farwell ............... 600/544 |
| 7,716,697 B2* | 5/2010 | Morikawa et al. ............. 725/10 |
| 7,739,140 B2 | 6/2010 | Vinson et al. |
| 7,742,623 B1 | 6/2010 | Moon et al. |
| 7,751,878 B1* | 7/2010 | Merkle et al. ................ 600/545 |
| 7,805,009 B2 | 9/2010 | Everett et al. |
| 7,853,122 B2* | 12/2010 | Miura et al. ........................ 725/10 |
| 7,914,468 B2* | 3/2011 | Shalon et al. ................ 600/590 |
| 7,942,816 B2 | 5/2011 | Satoh et al. |
| 2001/0016874 A1 | 8/2001 | Ono et al. |
| 2001/0056225 A1* | 12/2001 | DeVito ............... 600/300 |
| 2002/0107454 A1* | 8/2002 | Collura et al. ............. 600/544 |
| 2002/0154833 A1 | 10/2002 | Koch et al. |
| 2002/0182574 A1 | 12/2002 | Freer |
| 2002/0188216 A1 | 12/2002 | Kayyali et al. |
| 2003/0003433 A1 | 1/2003 | Carpenter et al. |
| 2003/0055355 A1 | 3/2003 | Viertio-Oja |
| 2003/0063780 A1 | 4/2003 | Gutta et al. |
| 2003/0066071 A1 | 4/2003 | Gutta et al. |
| 2003/0067486 A1 | 4/2003 | Lee et al. |
| 2003/0076369 A1 | 4/2003 | Resner |
| 2003/0081834 A1 | 5/2003 | Philomin et al. |
| 2003/0093784 A1 | 5/2003 | Dimitrova et al. |
| 2003/0126593 A1* | 7/2003 | Mault ............... 725/10 |
| 2003/0153841 A1 | 8/2003 | Kilborn et al. |
| 2004/0013398 A1 | 1/2004 | Miura et al. |
| 2004/0018476 A1 | 1/2004 | LaDue |
| 2004/0039268 A1 | 2/2004 | Barbour et al. |
| 2004/0072133 A1* | 4/2004 | Kullok et al. ............. 434/236 |
| 2004/0077934 A1* | 4/2004 | Massad ............... 600/300 |
| 2004/0088289 A1 | 5/2004 | Xu et al. |
| 2004/0111033 A1* | 6/2004 | Oung et al. .................. 600/483 |
| 2004/0161730 A1* | 8/2004 | Urman ............... 434/236 |
| 2004/0193068 A1* | 9/2004 | Burton et al. .................. 600/544 |
| 2004/0208496 A1 | 10/2004 | Pilu |
| 2004/0267141 A1 | 12/2004 | Amano et al. |
| 2005/0010087 A1 | 1/2005 | Banet |
| 2005/0010116 A1* | 1/2005 | Korhonen et al. ............. 600/481 |
| 2005/0043774 A1 | 2/2005 | Devlin et al. |
| 2005/0045189 A1 | 3/2005 | Jay |
| 2005/0066307 A1 | 3/2005 | Patel et al. |
| 2005/0071865 A1 | 3/2005 | Martins |
| 2005/0096311 A1 | 5/2005 | Suffin et al. |
| 2005/0097594 A1 | 5/2005 | O'Donnell et al. |
| 2005/0113656 A1 | 5/2005 | Chance |
| 2005/0120372 A1 | 6/2005 | Itakura |
| 2005/0143629 A1* | 6/2005 | Farwell ............... 600/300 |
| 2005/0165285 A1* | 7/2005 | Iliff ............... 600/300 |
| 2005/0172311 A1 | 8/2005 | Hjelt et al. |
| 2005/0223237 A1 | 10/2005 | Barletta et al. |
| 2005/0289582 A1 | 12/2005 | Tavares et al. |
| 2006/0010470 A1 | 1/2006 | Kurosaki et al. |
| 2006/0064037 A1* | 3/2006 | Shalon et al. ............. 600/586 |
| 2006/0094970 A1 | 5/2006 | Drew |
| 2006/0111621 A1 | 5/2006 | Coppi et al. |
| 2006/0143647 A1* | 6/2006 | Bill ............... 725/10 |
| 2006/0217598 A1* | 9/2006 | Miyajima et al. ............. 600/300 |
| 2006/0258926 A1 | 11/2006 | Ali et al. |
| 2006/0265022 A1* | 11/2006 | John et al. ............... 607/45 |
| 2006/0277102 A1 | 12/2006 | Agliozzo |
| 2006/0293608 A1 | 12/2006 | Rothman et al. |
| 2006/0293921 A1* | 12/2006 | McCarthy et al. ............. 705/2 |
| 2007/0031798 A1* | 2/2007 | Gottfried ............... 434/236 |
| 2007/0048707 A1 | 3/2007 | Caamano et al. |
| 2007/0053513 A1 | 3/2007 | Hoffberg |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066914 A1* | 3/2007 | Le et al. ............. 600/544 |
| 2007/0116037 A1 | 5/2007 | Moore |
| 2007/0168461 A1 | 7/2007 | Moore |
| 2007/0173733 A1* | 7/2007 | Le et al. ............. 600/544 |
| 2007/0179396 A1 | 8/2007 | Le et al. |
| 2007/0184420 A1 | 8/2007 | Mathan et al. |
| 2007/0225585 A1 | 9/2007 | Washbon et al. |
| 2007/0235716 A1 | 10/2007 | Delic et al. |
| 2007/0238945 A1 | 10/2007 | Delic et al. |
| 2007/0265507 A1 | 11/2007 | De Lemos |
| 2008/0039737 A1 | 2/2008 | Breiter et al. |
| 2008/0091512 A1 | 4/2008 | Marci et al. |
| 2008/0144882 A1 | 6/2008 | Leinbach et al. |
| 2008/0159365 A1 | 7/2008 | Dubocanin et al. |
| 2008/0162182 A1 | 7/2008 | Cazares et al. |
| 2008/0177197 A1 | 7/2008 | Lee et al. |
| 2008/0201731 A1 | 8/2008 | Howcroft |
| 2008/0211768 A1 | 9/2008 | Breen et al. |
| 2008/0218472 A1* | 9/2008 | Breen et al. .................. 345/156 |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0062629 A1 | 3/2009 | Pradeep et al. |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0082643 A1 | 3/2009 | Pradeep et al. |
| 2009/0083129 A1 | 3/2009 | Pradeep et al. |
| 2009/0105576 A1 | 4/2009 | Do et al. |
| 2009/0112077 A1 | 4/2009 | Nguyen et al. |
| 2009/0156925 A1 | 6/2009 | Jin et al. |
| 2009/0214060 A1 | 8/2009 | Chuang et al. |
| 2009/0222330 A1 | 9/2009 | Leinbach |
| 2010/0076333 A9* | 3/2010 | Burton et al. ............. 600/544 |

(56) References Cited

U.S. PATENT DOCUMENTS

FOREIGN PATENT DOCUMENTS

| EP | 1607842 | 12/2005 |
|---|---|---|
| JP | 05293172 | 11/1993 |
| JP | 07-329657 | 12/1995 |
| JP | 2002-000577 | 1/2002 |
| JP | 0256500 | 2/2002 |
| JP | 2002-344904 | 11/2002 |
| JP | 2003-016095 | 1/2003 |
| JP | 2003-111106 | 4/2003 |
| JP | 2003-178078 | 6/2003 |
| JP | 2003522580 | 7/2003 |
| JP | 2005084770 | 3/2005 |
| JP | 2006-323547 | 11/2006 |
| KR | 10-2000-0072489 | 12/2000 |
| KR | 10-2001-0104579 | 11/2001 |
| WO | 00/17824 | 3/2000 |
| WO | 01/97070 | 12/2001 |
| WO | 2004100765 | 11/2004 |
| WO | 2006005767 | 1/2006 |
| WO | 2007/019584 | 2/2007 |

OTHER PUBLICATIONS

Form PCT/ISA/210, PCT/US07/15019, "PCT International Search Report," 2 pgs.
Form PCT/ISA/237, PCT/US07/15019, "PCT Written Opinion of the International Searching Authority," 5 pgs.
Form PCT/IB/326, PCT/US07/015019, "Notification Concerning Transmittal of International Preliminary Report on Patentability."
Form PCT/IB/373, PCT/US07/15019, "International Preliminary Report on Patentability."
Form PCT/ISA/220, PCT/US07/14955, "PCT Notification of Transmittal of the International Search Report and the Written Opinion of the International Searching Authority, or the Declaration," 1 pg.
Form PCT/ISA/210, PCT/US07/14955, "PCT International Search Report," 2 pgs.
Form PCT/ISA/237, PCT/US07/14955, "PCT Written Opinion of the International Searching Authority," 6 pgs.
Form PCT/IB/326, PCT/US07/14955, "Notification Concerning Transmittal of International Preliminary Report on Patentability." 1 page.
Form PCT/IB/373, PCT/US07/14955, "International Preliminary Report on Patentability." 1 page.
Form PCT/ISA/220, PCT/US07/16796, "PCT Notification of Transmittal of the International Search Report and the Written Opinion of the International Searching Authority, or the Declaration," 1 pg.
Form PCT/ISA/210, PCT/US07/16796, "PCT International Search Report," 2 pgs.
Form PCT/ISA/237, PCT/US07/16796, "PCT Written Opinion of the International Searching Authority," 6 pgs.
Form PCT/IB/326, PCT/US07/16796, "Notification Concerning Transmittal of International Preliminary Report on Patentability." 1 page.
Form PCT/IB/373, PCT/US07/16796, "International Preliminary Report on Patentability." 1 page.
Form PCT/ISA/220, PCT/US06/31569, "PCT Notification of Transmittal of the International Search Report and the Written Opinion of the International Searching Authority, or the Declaration," 1 pg.
Form PCT/ISA/210, PCT/US06/31569, "PCT International Search Report," 3 pgs.
Form PCT/ISA/237, PCT/US06/31569, "PCT Written Opinion of the International Searching Authority," 6 pgs.
Form PCT/IB/326, PCT/US06/31569, "Notification Concerning Transmittal of International Preliminary Report on Patentability." 1 page.
Form PCT/IB/373, PCT/US06/31569, "International Preliminary Report on Patentability." 1 page.
Form PCT/ISA/220, PCT/US07/20714, "PCT Notification of Transmittal of the International Search Report and the Written Opinion of the International Searching Authority, or the Declaration," 1 pg.
Form PCT/ISA/210, PCT/US07/20714, "PCT International Search Report," 2 pgs.
Form PCT/ISA/237, PCT/US07/20714, "PCT Written Opinion of the International Searching Authority," 6 pgs.
Form PCT/IB/326, PCT/US07/20714, "Notification Concerning Transmittal of International Preliminary Report on Patentability." 1 page.
Form PCT/IB/373, PCT/US07/20714, "International Preliminary Report on Patentability." 1 page.
Form PCT/ISA/220, PCT/US07/17764, "PCT Notification of Transmittal of the International Search Report and the Written Opinion of the International Searching Authority, or the Declaration," 1 pg.
Form PCT/ISA/210, PCT/US07/17764, "PCT International Search Report," 2 pgs.
Form PCT/ISA/237, PCT/US07/17764, "PCT Written Opinion of the International Searching Authority," 7 pgs.
Form PCT/IB/326, PCT/US07/17764, "Notification Concerning Transmittal of International Preliminary Report on Patentability." 1 page.
Form PCT/IB/373, PCT/US07/17764, "International Preliminary Report on Patentability." 1 page.
Form PCT/ISA/220, PCT/US07/20713, "PCT Notification of Transmittal of the International Search Rep;ort and the Written Opinion of the International Searching Authority, or the Declaration," 1 pg.
Form PCT/ISA/210, PCT/US07/20713, "PCT International Search Report," 2 pgs.
Form PCT/ISA/237, PCT/US07/20713, "PCT Written Opinion of the International Searching Authority," 5 pgs.
Form PCT/IB/326, PCT/US07/20713, "Notification Concerning Transmittal of International Preliminary Report on Patentability." 1 page.
Form PCT/IB/373, PCT/US07/20713, "International Preliminary Report on Patentability." 1 page.
Form PCT/ISA/220, PCT/US08/09110, "PCT Notification of Transmittal of the International Search Report and the Written Opinion of the International Searching Authority, or the Declaration," 1 pg.
Form PCT/ISA/210, PCT/US08/09110, "PCT International Search Report," 3 pgs.
Form PCT/ISA/237, PCT/US08/09110, "PCT Written Opinion of the International Searching Authority," 4 pgs.
Form PCT/ISA/220, PCT/US08/75640, "PCT Notification of Transmittal of the International Search Report and the Written Opinion of the International Searching Authority, or the Declaration," 1 pg.
Form PCT/ISA/210, PCT/US08/75640, "PCT International Search Report," 2 pgs.
Form PCT/ISA/237, PCT/US08/75640, "PCT Written Opinion of the International Searching Authority," 3 pgs.
Form PCT/ISA/220, PCT/US08/78633, "PCT Notification of Transmittal of the International Searching Report and the Written Opinion of the International Searching Authority, or the Delcaration," 1 pg.
Form PCT/ISA/210, PCT/US08/78633, "PCT International Search Report," 2 pgs.
Form PCT/ISA/237, PCT/US08/78633, "PCT Written Opinion of the International Searching Authority," 6 pgs.
Form PCT/ISA/220, PCT/US08/82147, "PCT Notification of Transmittal of the International Search Report and the Written Opinion of the International Searching Authority, or the Declaration," 1 pg.
Form PCT/ISA/210, PCT/US08/82147, "PCT International Search Report," 2 pgs.
Form PCT/ISA/237, PCT/US08/82147, "PCT Written Opinion of the International Searching Authority," 13 pgs.
Form PCT/ISA/220, PCT/US08/82149, "PCT Notification of Transmittal of the International Search Report and the Written Opinion of the International Searching Authority, or the Declaration," 1 pg.
Form PCT/ISA/210, PCT/US08/82149, "PCT International Search Report," 2 pgs.
Form PCT/ISA/237, PCT/US08/82149, "PCT Written Opinion of the International Searching Authority," 14 pgs.
Form PCT/ISA/220, PCT/US08/75651, "PCT Notification of Transmittal of the International Search Report and the Written Opinion of the International Searching Authority, or the Declaration," 1 pg.
Form PCT/ISA/210, PCT/US08/75651, "PCT International Search Report," 2 pgs.

(56) References Cited

OTHER PUBLICATIONS

Form PCT/ISA/237, PCT/US08/75651, "PCT Written Opinion of the International Searching Authority," 9 pgs.
Form PCT/ISA/220, PCT/US08/85723, "PCT Notification of Transmittal of the International Search Report and the Written Opinion of the International Searching Authority, or the Declaration," 1 pg.
Form PCT/ISA/210, PCT/US08/85723, "PCT International Search Report," 2 pgs.
Form PCT/ISA/237, PCT/US08/85723, "PCT Written Opinion of the International Searching Authority," 7 pgs.
Form PCT/ISA/220, PCT/US08/85203, "PCT Notification of Transmittal of the International Search Report and the Written Opinion of the International Searching Authority, or the Declaration," 1 pg.
Form PCT/ISA/210, PCT/US08/85203, "PCT International Search Report," 2 pgs.
Form PCT/ISA/237, PCT/US08/85203, "PCT Written Opinion of the International Searching Authority," 6 pgs.
Form PCT/ISA/220, PCT/US08/75649, "PCT Notification of Transmittal of the International Search Report and the Written Opinion of the International Searching Authority, or the Declaration," 1 pg.
Form PCT/ISA/210, PCT/US08/75649, "PCT International Search Report," 3 pgs.
Form PCT/ISA/237, PCT/US08/75649, "PCT Written Opinion of the International Searching Authority," 5 pgs.
Technology Platform: SmartShirt + Eye-Tracking Innerscope Research, Mar. 2007.
Egner, Tobias; Emilie Strawson, and John H. Gruzelier, "EEG Signature and Phenomenology of Alpha/theta Neurofeedback Training Versus Mock Feedback." Applied Psychophysiology and Biofeedback. vol. 27, No. 4. Dec. 2002.
Clarke, Adam R. et al., EEG Analysis of Children with Attention-Deficit/Hyperactivity Disorder and Comorbid Reading Disabilities, Journal of Learning Disabilities, vol. 35, No. 3, (May-Jun. 2002), pp. 276-285.
Carter, R., "Mapping the Mind" 1998 p. 182 University of California Press, Berkley.
Harmony et al. (2004) Specific EEG frequencies signal general common cognitive processes as well as specific tasks processes in man. Int. Journal of Psychophysiology 53(3): 207-16.
Klimesch, W., Schimke, H., Schwaiger, J. (1994) Episodic and semantic memory: an analysis in the EEG theta and alpha band. Electroencephalography Clinical Neurophysiology.
Mizuhara, H.,Wang LQ, Kobayashi, K., Yamaguchi, Y., (2004) A long range cortical network emerging with theta oscillation in mental task. Neuroreport 15(8): 1233-1238.
Seldon, G (1981) "Machines that Read Minds." Science Digest, Oct.
Willis, M. & Hodson, V.; Discover Your Child's Learning Style: Children Learn in Unique Ways-Here's the Key to Every Child's Learning Success, Prime Publishing. Roseville, CA.
Wise, A (1996) The High Performance Mind, Mastering Brainwaves for Insight, Healing and Creativity. G.P. Putnam's Son, New York. pp. 13-15; 20-22; 143-156.
Wise, A (1996) The High Performance Mind, Mastering Brainwaves for Insight, Healing and Creativity. G.P. Putnam's Son, New York. pp. 156-158; 165-170; 186-187, 189-192.
El-Bab, M. (2001) Cognitive event related potentials during a learning task. Doctoral Dissertation, Faculty of Medicine, University of Southampton, UK.
Gevins et al. (1997) High resolution EEG mapping of cortical activation related to a working memory, Cereb Cortex. 7: 374-385.
Hughes, J.R. & John, E.R. (1999) Conventional and Quantitative Electroencephalography in Psychiatry. Journal of Neuropsychiatry and Clinical Neurosciences. vol. 11(2): 190-208.
International Search report and Written Opinion for PCT Application PCT/US07/020714, Search report dated Apr. 8, 2008, 11 pages (2008).
Final Decision of Rejection, English Language, issued by the Japanese Intellectual Property Office in connection with Japanese application No. 2009-552656, on Jan. 21, 2013, 3 pages.

Notice of Reason for Rejection, English Language, issued by the Japanese Intellectual Property Office in connection with Japanese application No. 2009-552660, on Mar. 13, 2013, 3 pages.
Notice of Panel Decision from Pre-Appeal Brief Review, issued by the United States Patent and Trademark Office in connection with U.S. Appl. No. 11/804,555, filed Mar. 25, 2013, 2 pages.
Advisory Action, issued by the United States Patent and Trademark Office in connection with U.S. Appl. No. 11/804,555, filed Mar. 6, 2013, 3 pages.
European Office Action, issued by the European Patent Office in connection with European Patent Application No. 07 838 838.6-2319, on Sep. 23, 2011, 4 pages.
W. Klimesch, "EEG alpha and theta oscillation reflect cognitive and memory performance: a review and analysis," Brain Research Reviews 29, Elsevier Science B.V., 1999, pp. 169-195.
Interrogative Statement, English Language, issued by the Intellectual Property Office of Japan, in connection with Japanese application No. 2009-552656, on Oct. 25, 2013, 4 pages.
European Office Action, issued by the European Patent Office in connection with European Patent Application No. 07796518.4, on Sep. 13, 2013, 7 pages.
European Office Action, issued by the European Patent Office in connection with European Patent Application No. 07838838.6, on Oct. 23, 2013, 4 pages.
Office Action, issued by the United States Patent and Trademark Office in connection with U.S. Appl. No. 13/553,515 on Jul. 17, 2013, 12 pages.
Notification of Grant of Patent Right for Invention, issued by the State Intellectual Property Office of the P.R. China, in connection with Chinese Patent Application No. 200780052869.9, on Aug. 31, 2012, 1 page.
Notification of the Third Office Action, issued by the State Intellectual Property Office of the P.R. China, in connection with Chinese Patent Application No. 200780052868.4, on Aug. 9, 2012, 7 pages.
Notification of the Second Office Action, issued by the State Intellectual Property Office of the P.R. China, in connection with Chinese Patent Application No. 200780052879.2, on May 4, 2012, 11 pages.
Notification of the Third Office Action, issued by the State Intellectual Property Office of the P.R. China, in connection with Chinese Patent Application No. 200680031159.3, on Mar. 28, 2012, 6 pages.
Notification of the Second Office Action, issued by the State Intellectual Property Office of the P.R. China, in connection with Chinese Patent Application No. 200680031159.3, on Oct. 19, 2011, 8 pages.
Notification of the Third Office Action, issued by the State Intellectual Property Office of the P.R. China, in connection with Chinese Patent Application No. 200780052879.2, on Dec. 31, 2012, 10 pages.
European Office Action, issued by the European Patent Office in connection with European Patent Application 07 838 838.6, on Sep. 5, 2012, 5 pages.
Supplemental European Search Report, issued by the European Patent Office in connection with European Patent Application No. 07796518.4, on Jul. 11, 2012, 8 pages.
European Office Action, issued by the European Patent Office in connection with European Patent Application No. 07 810 808.1, on Dec. 1, 2011, 6 pages.
Supplemental European Search Report, issued by the European Patent Office in connection with European Patent Appliation No. 06824810.3, on Nov. 22, 2011, 14 pages.
European Office Action, issued by the European Patent Office in connection with European Patent Application No. 07 852 430.3, on Mar. 6, 2012, 5 pages.
Supplemental European Search Report, issued by the European Patent Office in connection with European Patent Application No. 07811241.4, on Feb. 14, 2012, 6 pages.
European Office Action, issued by the European Patent Office in connection with European Patent Application No. 07 838 838.6, on Sep. 23, 2011, 4 pages.
Supplemental European Search Report, issued by the European Patent Office in connection with European Patent Application No. 06824810.3, on Nov. 3, 2011, 13 pages.
Supplemental European Search Report, issued by the European Patent Office in connection with European Patent Application No. 07796518.4, on Jul. 30, 2012, 9 pages.

(56) References Cited

OTHER PUBLICATIONS

Notification of Reason(s) for Rejection, issued by the Japanese Intellectual Property Office in connection with Japanese Patent Application No. 2009-552658, on Apr. 19, 2012, 2 pages.
Notification of Reason(s) for Rejection, issued by the Japanese Intellectual Property Office in connection with Japanese Patent Application No. 2009-552657, on May 2, 2012, 5 pages.
Notification of Reason(s) for Rejection, issued by the Japanese Intellectual Property Office in connection with Japanese Patent Application No. 2009-552656, on Mar. 30, 2012, 3 pages.
Notification of Reasons(s) for Rejection, issued by the Japanese Intellectual Property Office in connection with Japanese Patent Application No. 2008-529085, Nov. 29, 2011, 2 pages.
Notification of Reasons(s) for Rejection, issued by the Japanese Intellectual Property Office in connection with Japanese Patent Application No. 2009-552661, Nov. 13, 2012, 3 pages.
Notification of Reasons(s) for Rejection, issued by the Japanese Intellectual Property Office in connection with Japanese Patent Application No. 2009-552659, Nov. 16, 2012, 4 pages.
Notification of Reasons(s) for Rejection, issued by the Japanese Intellectual Property Office in connection with Japanese Patent Application No. 2009-552660, Nov. 16, 2012, 3 pages.
Notice of Allowance and Fee(s) Due, issued by the United States Patent and Trademark Office in connection with U.S. Appl. No. 11/804,517, on Mar. 21, 2012, 8 pages.
Final Rejection, issued by the United States Patent and Trademark Office in connection with U.S. Appl. No. 11/804,517, on Sep. 1, 2011, 11 pages.
Office Action, issued by the United States Patent and Trademark Office in connection with U.S. Appl. No. 11/804,517, on Feb. 3, 2011, 15 pages.
Final Rejection, issued by the United States Patent and Trademark Office in connection with U.S. Appl. No. 11/804,517, on Jun. 23, 2010, 14 pages.
Office Action, issued by the United States Patent and Trademark Office in connection with U.S. Appl. No. 11/804,517, on Sep. 17, 2009, 15 pages.
Office Action, issued by the United States Patent and Trademark Office in connection with U.S. Appl. No. 11/804,555, on Mar. 15, 2012, 15 pages.
Final Rejection, issued by the United States Patent and Trademark Office in connection with U.S. Appl. No. 11/804,555, on Oct. 9, 2012, 11 pages.
Final Rejection, issued by the United States Patent and Trademark Office in connection with U.S. Appl. No. 11/804,555, on Jul. 21, 2010, 14 pages.
Office Action, issued by the United States Patent and Trademark Office in connection with U.S. Appl. No. 11/804,555, on Oct. 1, 2009, 17 pages.
Office Action, issued by the United States Patent and Trademark Office in connection with U.S. Appl. No. 11/779,814, on Feb. 13, 2012, 19 pages.
Final Rejection, issued by the United States Patent and Trademark Office in connection with U.S. Appl. No. 11/779,814, on Jun. 28, 2012, 18 pages.
Final Rejection, issued by the United States Patent and Trademark Office in connection with U.S. Appl. No. 11/779,814, on Jun. 18, 2010, 24 pages.
Office Action, issued by the United States Patent and Trademark Office in connection with U.S. Appl. No. 11/779,814, on Oct. 5, 2009, 24 pages.
Final Rejection, issued by the United States Patent and Trademark Office in connection with U.S. Appl. No. 11/500,678, on Dec. 8, 2010, 9 pages.
Office Action, issued by the United States Patent and Trademark Office in connection with U.S. Appl. No. 11/500,678, on Mar. 17, 2010, 10 pages.
Office Action, issued by the United States Patent and Trademark Office in connection with U.S. Appl. No. 11/500,678, on Sep. 3, 2008, 12 pages.
Final Rejection, issued by the United States Patent and Trademark Office in connection with U.S. Appl. No. 11/500,678, on , Jun. 9, 2009, 11 pages.
Final Rejection, issued by the United States Patent and Trademark Office in connection with U.S. Appl. No. 11/835,634, on Apr. 25, 2012, 23 pages.
Office Action, issued by the United States Patent and Trademark Office in connection with U.S. Appl. No. 11/835,634, on Sep. 1, 2011, 16 pages.
Final Rejection, issued by the United States Patent and Trademark Office in connection with U.S. Appl. No. 12/206,676, on Mar. 6, 2012, 9 pages.
Office Action, issued by the United States Patent and Trademark Office in connection with U.S. Appl. No. 12/206,676, on May 10, 2011, 9 pages.
Final Rejection, issued by the United States Patent and Trademark Office in connection with U.S. Appl. No. 12/206,702, on Jun. 3, 2010, 8 pages.
Office Action, issued by the United States Patent and Trademark Office in connection with U.S. Appl. No. 12/206,702, on May 28, 2009, 8 pages.
Final Rejection, issued by the United States Patent and Trademark Office in connection with U.S. Appl. No. 11/681,265, on Apr. 10, 2012, 18 pages.
Office Action, issued by the United States Patent and Trademark Office in connection with U.S. Appl. No. 11/681,265, on Jun. 21, 2011, 15 pages.
Restriction and/or Election Requirement, issued by the United States Patent and Trademark Office in connection with U.S. Appl. No. 11/846,068, on Feb. 21, 2012, 6 pages.
Office Action, issued by the United States Patent and Trademark Office in connection with U.S. Appl. No. 11/846,068, on Apr. 27, 2012, 9 pages.
Notice of Allowance and Fee(s) Due, issued by the United States Patent and Trademark Office in connection with U.S. Appl. No. 11/846,068, on Dec. 26, 2012, 9 pages.
Office Action, issued by the United States Patent and Trademark Office in connection with U.S. Appl. No. 12/835,714, on Jan. 22, 2013, 34 pages.
Adamic et al., "The political blogosphere and the 2004 U.S. election: Divided they blog," Proceedings WWW-2005 2nd Annual Workshop on the Weblogging Ecosystem, 2005, Chiba, Japan, 16 pages.
Adar et al., "Implicit structure and the dynamics of blogspace," Proceedings WWW-2004 Workshop on the Weblogging Ecosystem, 2004, New York, NY, 8 pages.
Aliod et al., "A Real World Implementation of Answer Extraction," Department of Computer Science, University of Zurich, Winterthurerstr. 190, CH-8057 Zurich, Switzerland, 6 pages.
Bishop, Mike, "Arrow Question/Answering Systems," Language Computer Corporation, 1999, 3 pages.
Bizrate, archived version of www.bizrate.com, Jan. 1999, 22 pages.
Blum, "Empirical Support for Winnow and Weighted-Majority Algorithms: Results on a Calendar Scheduling Domain," in Machine Learning, vol. 26, Kluwer Academic Publishers, Boston, USA, 1997, 19 pages.
Bournellis, Cynthia, "Tracking the hits on Web Sites," Communications International: vol. 22, Issue 9, London, Sep. 1995, 3 pages.
Chaum et al., "A Secure and Privacy-Protecting Protocol for Transmitting Personal Information Between Organizations," A.M. Odlyzko (Ed.): Advances in Cryptology, CRYPTO '86, LNCS 263, 1987, 51 pages.
Chaum, David L., "Untraceable Electronic Mail, Return Addresses, and Digital Pseudonymns," Communication of the ACM, vol. 24, No. 2, 1981, 5 pages.
Cohen, William W., "Data Integration using similarity joins and a word-based information representation language," ACM Transactions on Information Systems, vol. 18, No. 3, Jul. 2000, 34 pages.
Cohn et al., "Active Learning with Statistical Models," Journal of Artificial Intelligence Research 4, AI Access Foundation and Morgan Kaufmann Publishers, USA, 1996, 17 pages.
Dagan et al., "Mistake-Driven Learning in Text Categorization," in EMNLP '97, $2^{nd}$ Conference on Empirical Methods in Natural Language Processing, 1997, 9 pages.

(56) References Cited

OTHER PUBLICATIONS

Delahaye Group, "Delahaye Group to Offer Nets Bench: High Level Web-Site Qualitative Analysis and Reporting; NetBench Builds on Systems provided by I/PRO and Internet Media Services," 1995 Business Wire, Inc., May 31, 1995, 3 pages.
Dialogic, www.dialogic.com as archived on May 12, 2000, 34 pages.
Dillon et al., "Marketing research in a Marketing Environment," Times Mirror/Mosby College, USA, 1987, 5 pages.
Ewatch, eWatch's archived web site retrieved from [URL: http://web.archive.org/web/19980522190526/wwww.ewatch.com] on Sep. 8, 2004, archived May 22, 1998, 50 pages.
Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.
Farber, Dave, "IP: eWatch and Cybersleuth," retrieved from [URL: http://www.interesting-people.org/archives/interesting-people/200006/msg00090.html] Jun. 29, 2000, 4 pages.
Freund et al., "Selective Sampling Using the Query by Committee Algorithm," Machine Learning 28 Kluwer Academic Publishers, The Netherlands, 1997, 36 pages.
Glance et al., "Analyzing online disussion for marketing intelligence," Proceedings WWW-2005 2nd Annual Workshop on the Weblogging Ecosystem, Chiba, Japan, 2005, 2 pages.
Glance et al., "Deriving marketing intelligence from online discussion," 11th ACM SIGKDD International Conference on Knowledge Discovery and Data Mining, Chicago, IL, Aug. 21-24, 2005, 10 pages.
Grefenstette et al., "Validating the Coverage of Lexical Resources for Affect Analysis and Automatically Classifying New Words along Semantic Axes," Chapter X, 3, Mar. 2004, 16 pages.
Harabagiu, Sanda M., "An Intelligent System for Question Answering," University of Southern California; Modlovan, Dan, Southern Methodist University, 1996, 5 pages.
Harabagiu, Sanda M., "Experiments with Open-Domain Textual Question Answering," Department of Computer Science and Engineering at Southern Methodist Universtity, 2000, 7 pages.
Harabagiu, Sanda M., "Mining Textual Answers with Knowledge-Based Indicators," Department of Computer Science and Engineering at Southern Methodist University, 2000, 5 pages.
Housley et al., "Internet X.509 Public Key Infrastructure Certificate and CRL Profile," Network Working Group Request for Comments: 2459, Jan. 1999, 121 pages.
Joachims, Thorsten, "Text Categorization with Support Vector Machines: Learning with Many Relevant Features," in Machine Learning: ECML-98, Tenth European Conference on Machine Learning, 1998, 7 pages.
Kahn et al., "Categorizing Web Documents using Competitive Learning: An ingrediant of a Personal Adaptive Agent," IEEE 1997, 4 pages.
Katz, Boris, "From Sentence Processing to Information Access on the World Wide Web," MIT Artificial Intelligence Laboratory, Feb. 27, 1997, 20 pages.
Kleppner, "Advertising Procedure," 6th edition, 1977, Prentice-Hall, Inc., Englewood Cliffs, NJ, p. 492, 3 pages.
Kotler, "Marketing Management," PrenticeHall International Inc., Upper Saddle River, NJ, 1997, 10 pages.
Klimesch, "EEG alpha and theta oscillations reflect cognitive and memory performance: a review and analysis," Brain Research Reviews, vol. 29, 1999, 27 pages.
Lenz et al., "Question answering with Textual CBR," Department of Computer Science, Humboldt University Berlin, D-10099 Berlin, 1998, 12 pages.
Littlestone, Nick, "Learning Quickly When Irrelevant Attributes Abound: A New Linear-threshold Algorithm," in Machine Learning, vol. 2, Kluwer Academic Publishers, Boston, MA, 1988, 34 pages.
Marlow, "Audience, structure and authority in the weblog community," International Communication Association Conference, MIT Media Laboratory, New Orleans, LA 2004, 9 pages.
McCallum et al., "Text Classification by Bootstrapping with the Keywords, EM and Shrinkage," Just Research and Carnegie Mellon University, Pittsburgh, PA, circa 1999, 7 pages.
McLachlan et al., "The EM Algorithm and Extensions," John Wiley & Sons, Inc., New York, NY, 1997, 301 pages.
Moldovan et al., "LASSO: A Tool for Surfing the Answer Net," Department of Computer Science and Engineering at Southern Methodist University, 1999, 9 pages.
Nakashima et al., "Information Filtering for the Newspaper," IEEE 1997, 4 pages.
Nanno et al., "Automatic collection and monitoring of Japanese Weblogs," Proceedings WWW-2004 Workshop on the weblogging Ecosystem, 2004, New York, NY, 7 pages.
Netcurrent, NetCurrent's web site, http://web.archive.org/web/20000622024845/www.netcurrents.com, retrieved on Jan. 17, 2005, archived on Jun. 22, 2000 and Sep. 18, 2000, 17 pages.
Pang et al., "Thumbs up? Sentiment Classification using Machine Learning Techniques," in Proceedings of EMNLP 2002, 8 pages.
Reguly, "Caveat Emptor Rules on the Internet," The Globe and Mail (Canada): Report on Business Column, Apr. 10, 1999, 2 pages.
Reinartz, "Customer Lifetime Value Analysis: An Integrated Empirical Framework for Measurement and Explanation," dissertation: Apr. 1999, 68 pages.
Schmidt et al., "Frontal brain electrical activity (EEG) distinguishes valence and intensity of musical emotions," Cognition and Emotion, vol. 15 (4), Psychology Press Ltd, 2001, 14 pages.
Sammler, "Music and emotion: Electrophysiological correlates of the processing of pleasant and unpleasant music," Psychophysiology, vol. 44, Blackwell Publishing Inc., 2007, 12 pages.
Soderland et al., "Customer Satisfaction and Links to Customer Profitability: An Empirical Examination of the Association Between Attitudes and Behavior," SSE/EFI Working Paper Series in Business Administration, Jan. 1999, 22 pages.
Thomas, "International Marketing," International Textbook Company, Scranton, PA 1971, 3 pages.
Trigaux, Robert, "Cyberwar Erupts Over Free Speech Across Florida, Nation," Knight-Ridder Tribune Business News, May 29, 2000, 4 pages.
Tull et al., "Marketing Research Measurement and Method," MacMillan Publishing Company, New York, NY, 1984, 9 pages.
Voorhees, Ellen M., "The TREC-8 Question Answering Track Report," National Institute of Standards and Technology, 1999, 6 pages.
Wiebe et al., "Identifying Collocations for Recognizing Opinions," in proceedings of ACL/EACL '01 Workshop on Collocation, Toulouse, France, Apr. 9, 2001, 9 pages.
Word of Mouth Research Case Study, "The Trans Fat Issue, Analysis of online consumer conversation to understand how the Oreo lawsuit impacted word-of-mouth on trans fats," Aug. 16, 2004, 35 pages.
Yang, "An Evaluation of Statistical Approaches to Text Categorization," Information Retrieval 1 (1/2) Apr. 10, 1999, 12 pages.
Zagat, www.zagat.com, archived on Apr. 29, 1999, 33 pages.
Zagat, www.zagat.com, archived version of p. 34, Feb. 1999, 1 page.
Group A: U.S. Appl. No. 11/804,517.
U.S. Appl. No. 13/553,515.
U.S. Appl. No. 11/804,555.
U.S. Appl. No. 11/779,814.
U.S. Appl. No. 11/500,678.
U.S. Appl. No. 11/845,993.
U.S. Appl. No. 11/835,634.
U.S. Appl. No. 11/846,068.
U.S. Appl. No. 12/206,676.
U.S. Appl. No. 12/206,702.
U.S. Appl. No. 11/681,265.
U.S. Appl. No. 12/835,714.
Group B: U.S. Appl. No. 12/180,510.
Group C: U.S. Appl. No. 11/430,555.
Group D: U.S. Appl. No. 11/852,189.
Group E: U.S. Appl. No. 12/244,737.
U.S. Appl. No. 12/244,748.
U.S. Appl. No. 13/252,910.
U.S. Appl. No. 12/263,331.
U.S. Appl. No. 12/244,751.

(56) References Cited

OTHER PUBLICATIONS

U.S. Appl. No. 12/244,752.
U.S. Appl. No. 12/263,350.
U.S. Appl. No. 12/326,016.
Group F: U.S. Appl. No. 13/053,016.
U.S. Appl. No. 13/053,043.
Group G: U.S. Appl. No. 13/053,097.
Group H: U.S. Appl. No. 13/464,591.
Group I: U.S. Appl. No. 12/206,700.
Group J: U.S. Appl. No. 11/959,399.
European office action, issued by the European Patent Office in connection with European patent application No. 07 852 430.3, on Feb. 6, 2013, 5 pages.
Office Action, issued by the United States Patent and Trademark Office in connection with U.S. Appl. No. 11/835,634, issued on Feb. 26, 2013, 24 pages.
Notice for Reasons for Rejection, English Language, issued by the Intellectual Property Office of Japan, in connection with Japanese application No. 2009-552661, on Apr. 24, 2013, 2 pages.
Decision of Rejection, English Language, issued by the State Intellectual Property Office of the P.R. China, in connection with Chinese application No. 2007800528791, on May 29, 2013, 11 pages.
Decision of Rejection, Chinese Language, issued by the State Intellectual Property Office of the P.R. China, in connection with Chinese application No. 2007800528791, on May 29, 2013, 7 pages.
Final Office Action, issued by the United States Patent and Trademark Office in connection with U.S. Appl. No. 11/835,634 on Jun. 20, 2013, 23 pages.
Decision of Rejection, English Language, issued by the State Intellectual Property Office of the P.R. China, in connection with Chinese application No. 201210063607.5, on Nov. 19, 2013, 10 pages.
Decision of Rejection, Chinese Language, issued by the State Intellectual Property Office of the P.R. China, in connection with Chinese application No. 201210063607.5, on Nov. 19, 2013, 6 pages.
Final Office Action, issued by the United States Patent and Trademark Office in connection with United States application No. 13/553,515 on Jan. 9, 2014, 13 pages.
First Office Action and Search Report, with English Language Version, issued by the State Intellectual Property Office of the Peoples' Republic of China, in connection with Chinese Patent Application No. 201210244954.8, on Jan. 2, 2014, 25 pages.
Non Final Office Action, issued by the United States Patent and Trademark Office in connection with U.S. Appl. No. 11/500,678 on Mar. 18, 2014, 10 pages.
European Office Action, issued by the European Patent Office in connection with European Patent Application No. 07 838838.6 on Mar. 12, 2014, 3 pages.
Notice of Allowance and Fee(s) Due, issued by the United States Patent and Trademark Office in connection with U.S. Appl. No. 11/804,555 on Mar. 3, 2014, 7 pages.
Notification of Reasons(s) for Rejection, issued by the Japanese Intellectual Property Office in connection with Japanese Patent Application No. 2009-552660 Jan. 21, 2014, 4 pages.
European Office Action, issued by the European Patent Office in connection with European Patent Application 07 852 430.3, on Feb. 3, 2014, 3 pages.
Notification of Reasons(s) for Rejection, issued by the Japanese Intellectual Property Office in connection with Japanese Patent Application No. 2012-152836, Jan. 14, 2014, 5 pages.

\* cited by examiner

300

Start

↓ calculating an engagement value of the individual for an event of a media
302

↓ comparing the engagement value with a reference value to determine a difference between the amount that the individual was engaged with the media and the reference value of the media
304

↓ saving the comparison as a measure defining a rating of the event of the media
306

↓

End

$\Theta\downarrow + \alpha\uparrow + HR\uparrow \rightarrow$ Engagement $\uparrow$ $\Theta\uparrow + \alpha\downarrow + HR\downarrow \rightarrow$ Engagement $\downarrow$

---

$HR \uparrow \rightarrow$ Engagement $\uparrow$ $HR \downarrow \rightarrow$ Engagement $\downarrow$ $\Theta\downarrow \rightarrow$ Engagement $\uparrow$ $\Theta\uparrow \rightarrow$ Engagement $\downarrow$ $\alpha\uparrow \rightarrow$ Engagement $\uparrow$ $\alpha\downarrow \rightarrow$ Engagement $\downarrow$ FIG. 9
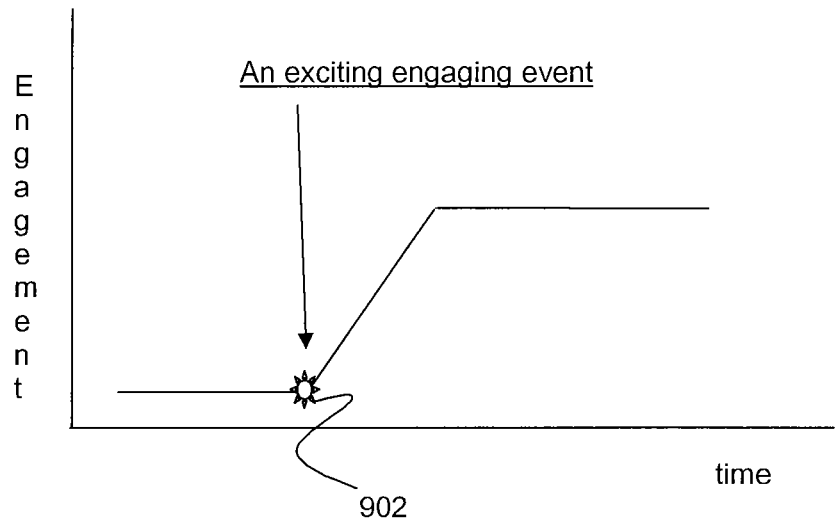
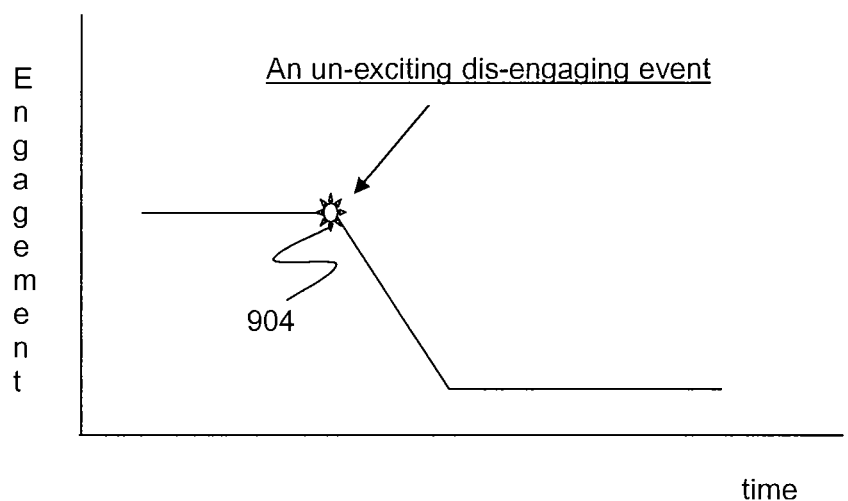

1100
FIG. 11
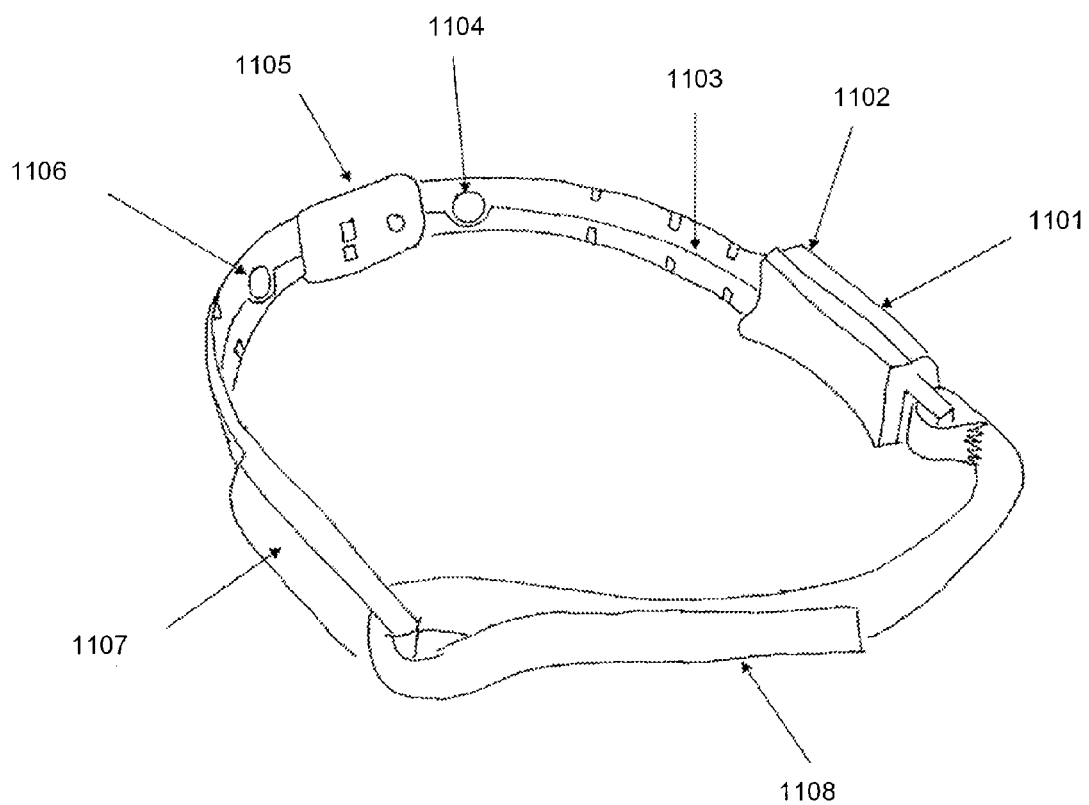

METHOD AND SYSTEM FOR MEASURING AND RANKING AN "ENGAGEMENT" RESPONSE TO AUDIOVISUAL OR INTERACTIVE MEDIA, PRODUCTS, OR ACTIVITIES USING PHYSIOLOGICAL SIGNALS

RELATED APPLICATIONS

This application claims priority to U.S. Provisional Patent Application No. 60/905,447, filed Mar. 8, 2007, and entitled "Method and system for measuring and ranking 'engagement' response to audiovisual or interactive media, products or activities using physiological signals" by Hans C. Lee, et al., which is incorporated by reference.

BACKGROUND OF THE INVENTION

Creative people design interactive media, activities and products ("media") that stimulate individuals and keep them engaged. Often times media are sold to consumers in highly competitive markets where the ability to stimulate engagement determines value. The creative people would like to know whether their customers are engaged in the media in order to maximize value by improving media to better stimulate individuals. If the value of the media is not maximized customers will purchase competing products which provide better stimulation. If competing products are sold, revenue will be lost as sales decline. A problem then is in providing accurate information about a response to stimulation by interactive media, activities, and products. Measuring the response requires creators of interactive media, activities and products to enter the minds of the target market.

In entering the human mind researchers in neurobiology, psychophysiology, and psychology found physiological signals emanating from the brain. Using the electroencephalogram (EEG) researchers recorded the physiological signals though electrodes attached to the head. The physiological signals had four main components below 30 hertz. Frequencies between 1-4 hertz were delta waves ($\delta$), frequencies between 4 and 8 hertz were theta ($\theta$) waves, frequencies between 8-13 hertz were alpha ($\alpha$) brainwaves, and frequencies between 13 and 20 were beta ($\beta$) brainwaves.

Additionally, tools used to collect data from the body include the photoplethysmograph (PPG), and the electrocardiogram (ECG or EKG, German electrocardiogram). The photoplethysmograph (PPG) is an optically obtained measurement which can be used to find the cardiac cycle. A PPG uses a pulse oximeter to observe a change in oxygen omission from the skin in relation to the cardiac cycle as blood is pumped to the extremities. The cardiac cycle can then be recorded based on this change in oxygen omission. Another measure of the heart rate is the ECG. The electrocardiogram (ECG), measures heartbeats via an electrode attached to the chest. Traditionally, an ECG produced an electrocardiograph, or a picture showing the heart beat over time. Alternatively, the signal generated by the heart is recorded.

The foregoing examples of the related art and limitations related therewith are intended to be illustrative and not exclusive. Other limitations of the related art will be come apparent to those of skill in the art upon a reading of the specification and a study of the drawings.

SUMMARY

The following embodiments and aspects thereof are described and illustrated in conjunction with systems, tools, and methods that are meant to be exemplary and illustrative, not limiting in scope. In various embodiments, one or more of the above described problems have been reduced or eliminated, while other embodiments are directed to other improvements.

A novel technique measures an "engagement" response of an individual to a media. The technique uses physiological signals emanating from the brain and the body to gauge the engagement response. An engagement value is an objective measure of the engagement response that quantifies an amount that a user is acting without thinking. Advantageously, the engagement response can be used to efficiently improve media while it is being created. In a non limiting example, ranking determines whether the individual finds a television show more engaging provoking than a documentary. Further, groups of individuals can have an engagement response that can be measured and aggregated to determine the overall population response to the media. This population view of the media can then be used to rank the media which is a novel use of physiological changes in response to media.

BRIEF DESCRIPTION OF THE DRAWINGS

Embodiments of the inventions are illustrated in the figures. However, the embodiments and figures are illustrative rather than limiting; they provide examples of the inventions.

FIG. 5 depicts a plurality of examples of formulas 500 related to ranking engagement.

FIG. 9 depicts graphs 900 of examples of changes in engagement relative to events in time.

FIG. 11 depicts a headset 1100 containing electrodes useful for collecting signals from a head of an individual as well as a heart signal.

DETAILED DESCRIPTION

In the following description, several specific details are presented to provide a thorough understanding of embodiments of the invention. One skilled in the relevant art will recognize, however, that the invention can be practiced without one or more of the specific details, or in combination with other components, etc. In other instances, well-known implementations or operations are not shown or described in detail to avoid obscuring aspects of various embodiments of the invention.

A novel system and method for measuring an "engagement" response for use in rating media uses physiological signals. An individual responds to a media while physiological sensors record this response. A processing component collects the physiological signals through the physiological sensors and substantially concurrently assigns an engagement value to the amount the individual acts without thinking. "Substantially concurrently" means that the response is at the same time or near in time to the stimulation. There may be a delay in the response. Therefore, the engagement value is calculated with the understanding that the response may be immediately following if not exactly at the same time with the stimulation.

In some embodiments, an exemplary way of calculating an engagement value is consider how much an individual is acting without thinking. Three useful signals for doing this include alpha waves and theta waves from a mind, and then a heart rate (HR). Other useful signals exist, and some of them will be discussed later on. Generally speaking, an increased heart rate is indicative of higher engagement, increased theta is indicative of higher levels of thought, thus lower engagement, and increased alpha is indicative of lower levels of thought, thus higher engagement. These exact relationships are explored in more depth in the discussion of FIG. 4 which depicts examples of formulas related to ranking engagement.

Figure 1:
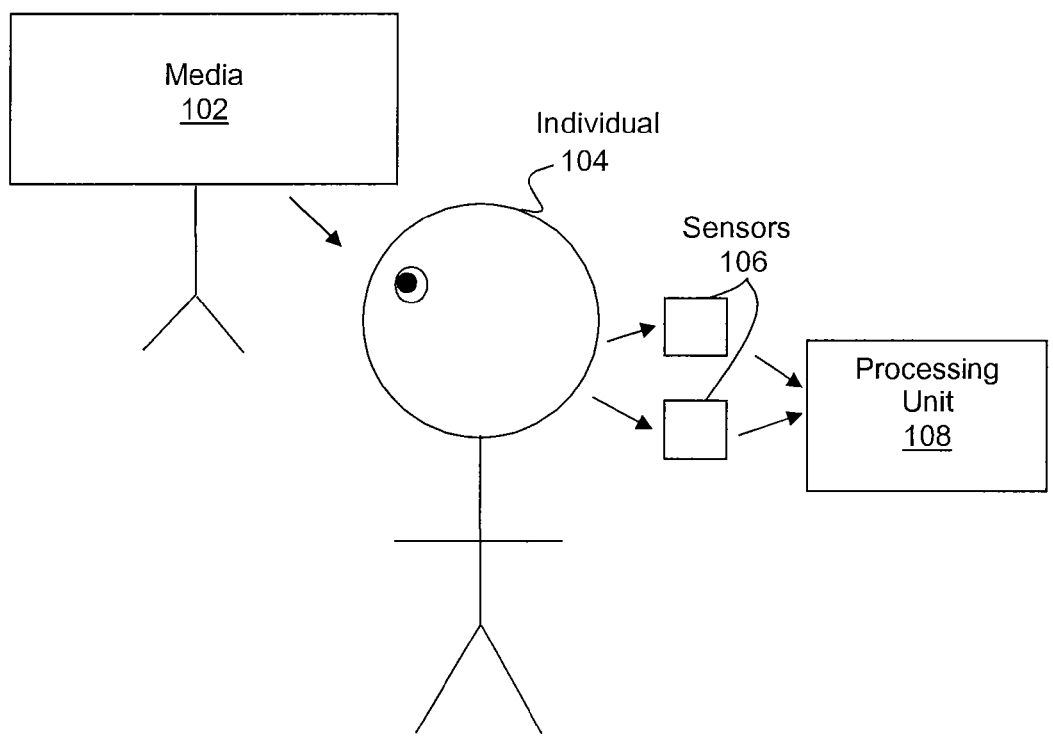
FIG. 1 is an illustration of an example of a system 100 for calculating an engagement value.

FIG. 1 is an illustration of an example of a system 100. In the example of FIG. 1, the system 100 includes media 102, individual 104, sensors 106, and processing component 108. As depicted, individual 104 is stimulated by media 102 while having the individual's engagement level monitored by processing component 108 using sensors 106. Here the media can be one or more of a movie, a video a television program, a commercial, an advertisement, a video game, an interactive online media, a print, or any other media which could stimulate an individual. Sensors 106 could be one or more of an accelerometer, a blood oxygen sensor, a galvanometer, an electroencephalogram, an electromyograph, and any other physiological sensor.

Figure 2:
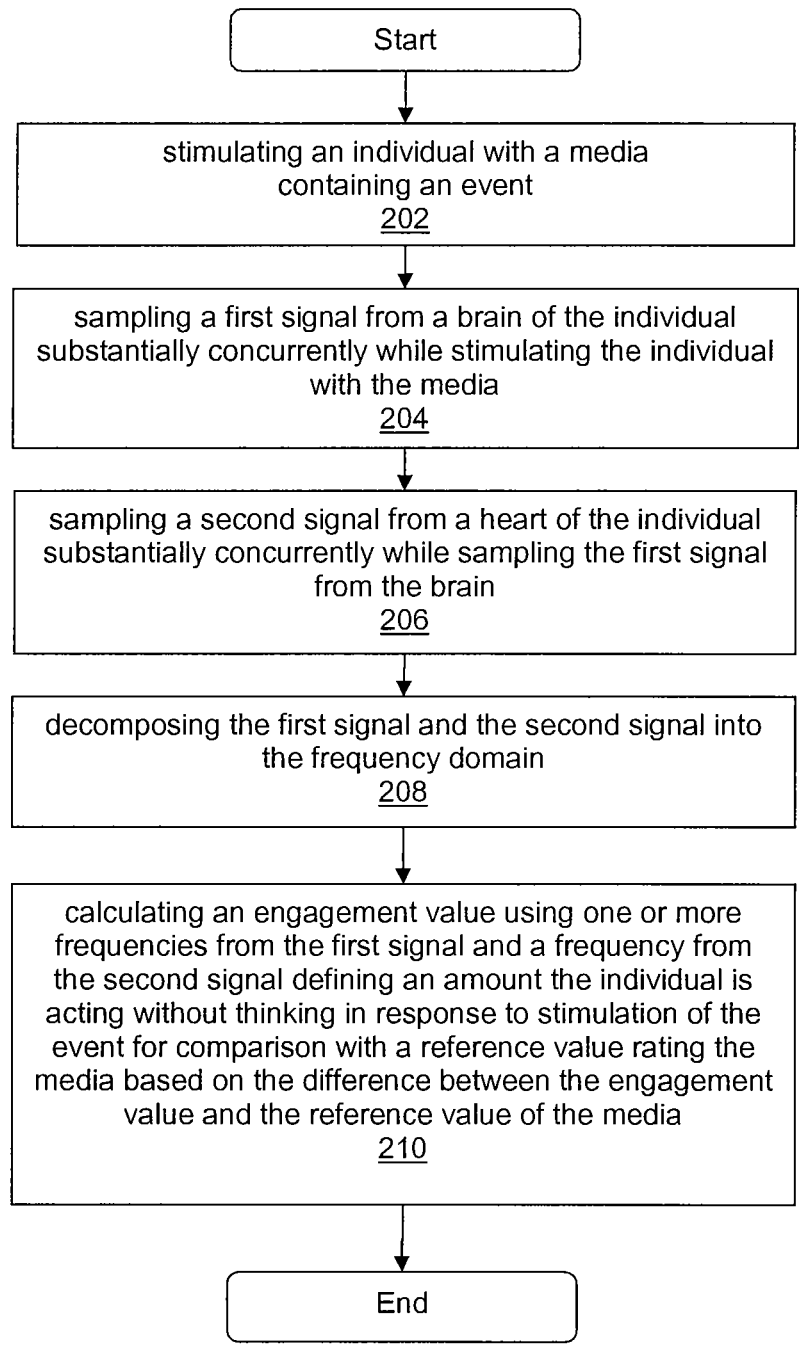
FIG. 2 depicts a flowchart 200 of an example of a method for calculating an engagement value based the amount that an individual is acting without thinking.

FIG. 2 depicts a flowchart 200 of an example of a method for calculating an engagement value. The method is organized as a sequence of modules in the flowchart 200. However, it should be understood that these and modules associated with other methods described herein may be reordered for parallel execution or into different sequences of modules. In the example of FIG. 2, the flowchart starts at module 202 with stimulating an individual with a media containing an event.

In the example of FIG. 2, the flowchart 200 continues to module 204 with sampling a first signal from a brain of the individual substantially concurrently while stimulating the individual with the media. The signal from the heart will include the heart rate. The signal from the heart is being concurrently collected using an electrode attached for that purpose. In calculating the heart rate, or number of heart beats per minute, one can determine a heart beat by finding the peak of the heart signal to the bottom of the heart signal. The exemplary headset discussed in reference to FIG. 11 could be used to both record the heart rate and brain waves.

In the example of FIG. 2, the flowchart 200 continues to module 206 with sampling a second signal from a heart of the individual substantially concurrently while sampling the first signal from the brain. The signal from the brain will include alpha and theta waves. Additionally, the signal from the brain will include other brain waves such as delta and theta waves. The frequency for the waves is approximately 1-4 Hz (delta) 4-8 Hz (theta), 8-13 Hz (alpha), 13-20 Hz (beta). The cut off point for a frequency range e.g. between alpha and beta, such as a cut off at 13 hz is approximate; one skilled in the art would apply the ranges with some interest in the various schools of thought in the science of psychophysiology. The examples of the algorithms provided herein can determine engagement by using any frequency or set of frequencies between 1 and 100 Hz in addition to a heart rate. It is possible to attach the electrodes to a head of an individual using a headset depicted in the example of FIG. 11. A chest electrode may be a simple electrode having adhesive to secure it to the skin and a wire to connect it to a device for collecting the heart rate.

In the example of FIG. 2, the flowchart 200 continues to module 208 decomposing the first signal and the second signal into the frequency domain. In this example, the fast Fourier transform (FFT), or wavelet analysis, both well known in the art of digital signal processing are used for the decomposition. FFT is an efficient method of computing the discrete Fourier transform (DFT); DFT could be used as well as other methods of computing Fourier analysis. In the alternative, wavelet analysis could be used to divide the signal into different frequency components so that they can be considered separately. Specifically, the morlet wavelet, the Mexican hat wavelet, a daubechies wavelet, a beta wavelet, or a coiflet wavelet would be useful for doing so. Other wavelets may be useful as well.

In some embodiments, the frequencies are separated out from the signal and stored into bins. In storing the frequencies from the signal, bins hold sampled signals from the frequency domain. A DFT bin can be defined by calculating an n point DFT. Specifically, n different sample values are created X(0) through X(n−1). With i being a value 0 to n−1, X(i) is a bin holding relevant sample values. The Alpha bin can hold anything between 8-13 Hz, but not necessarily including all frequencies in that range. The Theta bin can hold anything between 4-8 Hz, but does not have to include all frequencies. Similarly, delta and beta waves can be held in delta and beta bins. Additionally, the frequency profile can be adjusted to remove noise in the signal such as white noise or pink noise.

In the example of FIG. 2, the flowchart 200 continues to module 210 calculating an engagement value using the one or more frequencies from the first signal and a frequency from the second signal defining an amount the individual is acting without thinking in response to stimulation of the event for comparison with a reference value thereby rating the media based on the difference between the engagement value and the reference value of the media.

In some embodiments it is possible to sense engagement using only alpha, or only theta in contrast with the heart rate. Total EEG power is also useful. A single formula could be used to calculate an engagement value, wherein x/EEG represents x in contrast to total EEG power. Further, an optimized multiplier of theta could be used, such as by taking the natural log of theta and multiplying by a scale factor. In a non-limiting example theta could be optimized as: optimized theta=s~ln(theta) where s is a scale factor and ln(x) represents a function finding the natural log of x. Theta or optimized theta could be used in conjunction therewith In some embodiments alpha brainwaves are inversely correlated with cognitive activity. As alpha power increases there is a drop in thought; conversely as cortical processing increases, there is a drop in alpha power which is commonly referred to as alpha suppression. Using these bases, the engagement value is determined by using a formula which looks for an increasing heart rate, decreasing alpha power, and increasing theta power. An example of such a formula which is:

$$E = \frac{HR}{50} - \frac{\alpha - \theta}{\theta + \alpha}$$

This formula uses a combination of the heart rate, the alpha and the theta values. Specifically, a combination of alpha and theta values is subtracted from an adjusted heart rate which as been adjusted by dividing it by 50. The adjustment and the combination of alpha and theta values are non-limiting and the formula could be re-written as necessary for a particular application. Other formulas which could be used are discussed later in regard to FIG. 5 depicts a relationship between a heart rate and one of a plurality of example formulas useful for calculating an engagement value.

In some embodiments, one or more events of a media are used to define an engagement value for the media. An event is an identifiable portion of a media. It could be the punch line of a joke, or an important scene of a movie. An event of a media is measurable and can have an engagement value associated with it. A number of events will have a number of engagement values. The media can be ranked as a whole by considering the events it contains and engagement values associated with those events.

In some embodiments the engagement value is calculated at a specific point in time. An exemplary system produces a time variant graph of the engagement of the individual based on a plurality of engagement values calculated in reference to stimulation with a media.

In some embodiments, a derivative may be calculated to determine a change in engagement indicating a response to stimulus. In a non-limiting example an event of a media engages a person causing an engagement response which is identified by a positive derivative. A positive derivative indicates an increase in engagement and a negative derivative indicates a decrease in engagement. Creators of media could use this information to create media ware more engaging, or less engaging as the creators desire.

Figure 3:
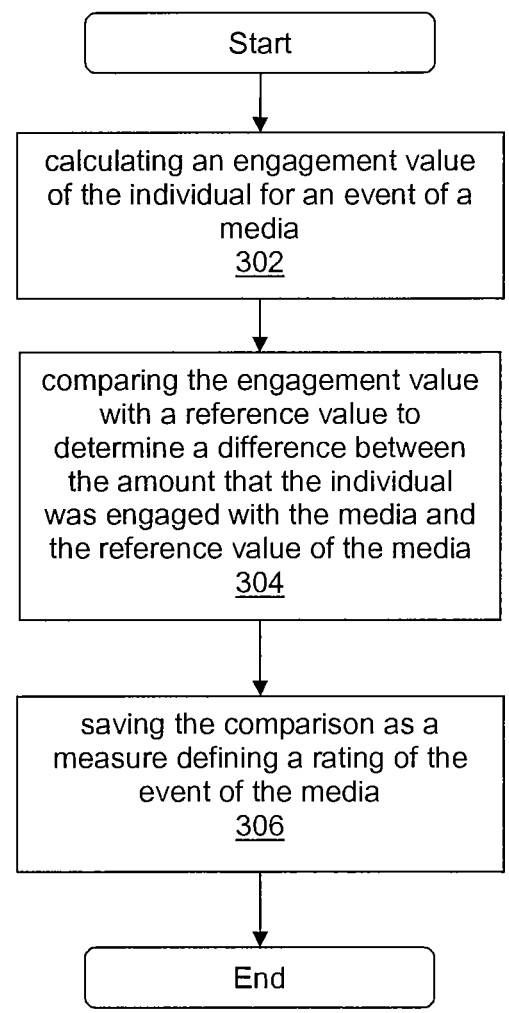
FIG. 3 depicts a flowchart of an example 300 of a method for ranking a first media against a second media based on engagement.

In some embodiments, a media may be ranked based on engagement values. FIG. 3 depicts a flowchart 300 of an example of a method for ranking a first media against a second media. Flowchart 300 starts at module 302 with calculating an engagement value of the individual for an event of a media. In acquiring the first engagement value, the first individual will be exposed to a media, and the data acquired may include a heart rate, alpha waves, theta waves, delta waves and beta waves. These values are gathered concurrently with respect to time. The data point will comprise the engagement value at this point in time. There may be a delay in the response, therefore the signal is sampled with the understanding that the response may be immediately following if not exactly temporal with the stimulation, thus it is substantially concurrent with the stimulation.

In some embodiments a reference value is used to compare a user engagement response to an event with a predetermined engagement value of the event. The reference value could be anything developed for the purpose of providing a comparison value from which to determine a difference between the user's engagement value and the event. Developers of media may create their own reference values. A reference value may be an ideal value i.e. a goal desired. A reference value could be the average of a number of different user engagement values calculated solely for the purpose of developing a reference value from which to compare other individuals.

In the example of FIG. 3, the flowchart 300 proceeds to module 304, with comparing the engagement value with a reference value to determine the difference between the amount that the individual was engaged with the media and the reference value of the media. The reference value can be acquired in the same manner as the first data point. Alternatively, it is supplied by a creator of the media.

Figure 4:
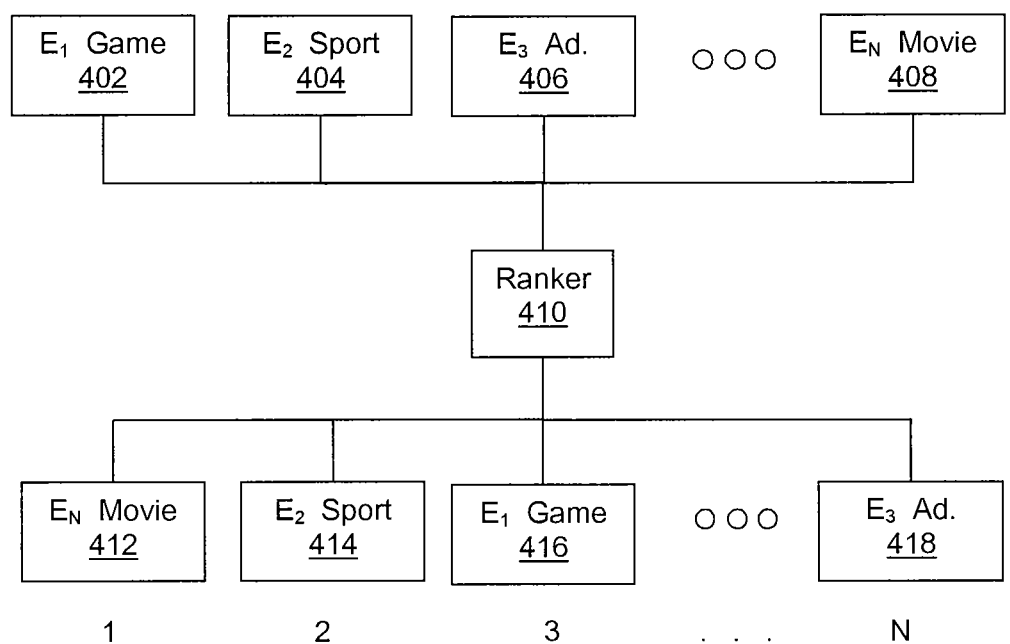
FIG. 4 depicts a diagram 400 of an example of ranking a plurality of media based on an engagement value.

In the example of FIG. 3, the flowchart 300 proceeds to module 306 with saving the comparison as a measure defining a rating of the event of the media. The relative difference between the engagement value and the reference value will be used to determine that an individual is relatively more engaged in, or less engaged in the media than the reference value. The relative difference can be used to rank a plurality of different media such as is depicted in FIG. 4.

In some embodiments, a plurality of media is ranked according to engagement values. In the example of FIG. 4, the diagram 400 of an example of ranking a plurality of media takes in n different media and ranks them in order relative to the engagement value associated with an individual. This could be extended to a group of individuals as is discussed relative to FIG. 8 where an average engagement value, or highest engagement value or other statistically motivated engagement value could be used to compare one media with another. In the original order at the top of diagram 400, the media are unorganized: the game 402, then the sport 404, then the Ad. 406, and then the Movie 408. Once the media have been ranked according to the related engagement values E1, E2 . . . EN. The relative rankings can be viewed as ranked Movie 412, then ranked Sport 414, then ranked game 416, then ranked Ad. 418. The ranking may be used to determine which media is the most engaging of the plurality of media, which is the least engaging, and other statistical measures of relative engagement of an individual with a media.

FIG. 5 depicts a plurality of formulas 500 related to ranking engagement. As discussed relative to FIG. 1, the relationship between theta, alpha, and heart rate determines the amount that an individual is acting without thinking, and thus the engagement of that individual. Decreasing theta waves are indicative of a decreasing level of engagement. Increasing alpha waves are indicative of a lower level of engagement. This increase in alpha and or relative decrease in theta is indicative of a change in level of engagement. An increased heart rate is associated with a level of excitement as is experienced when an individual's heart "races" in response to an exciting event. The combination thereof is the basis for finding that an individual is engaged with the media that the individual is interacting with. It is not sufficient to state that the individual theta, alpha, and heart rate changes are sufficient to determine a change in engagement, however, the change in one of the values is associated with a change in the engagement value, and correlated change of all the values involved may indicate a change in engagement.

Figure 6:
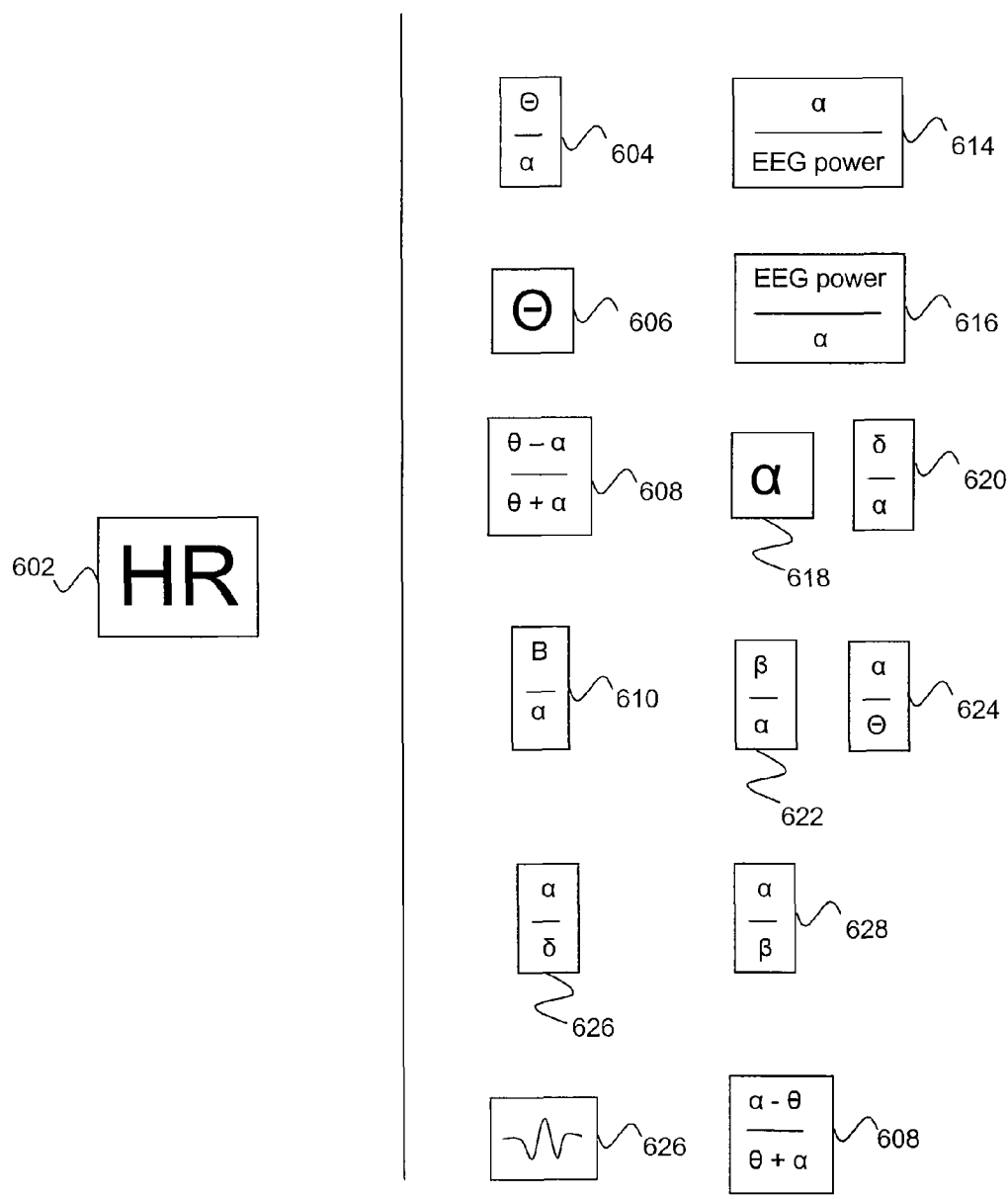
FIG. 6 depicts a relationship 600 between a heart rate and one of a plurality of example formulas useful for calculating an engagement value.

FIG. 6 depicts an example of a relationship 600 between a heart rate and one of a plurality of example formulas useful for calculating an engagement value. Relationship 600 includes heart rate (HR) 602, and formulas 604 through formula 628. Formula 626 denotes the predominating pulse width from a wavelet analysis. In calculating an engagement value, a formula may take into account HR and one or more of the formulas. The formula and the HR may each or both be multiplied or divided by constant values to adjust them for specific applications. Individual variables in one or more of the formulas may similarly be adjusted by constant values without similarly adjusting other variables in the formulas.

The relationship between the HR and the formula is used to determine engagement. Formulas not depicted but complying with the spirit of these teachings are similarly included.

Figure 7:
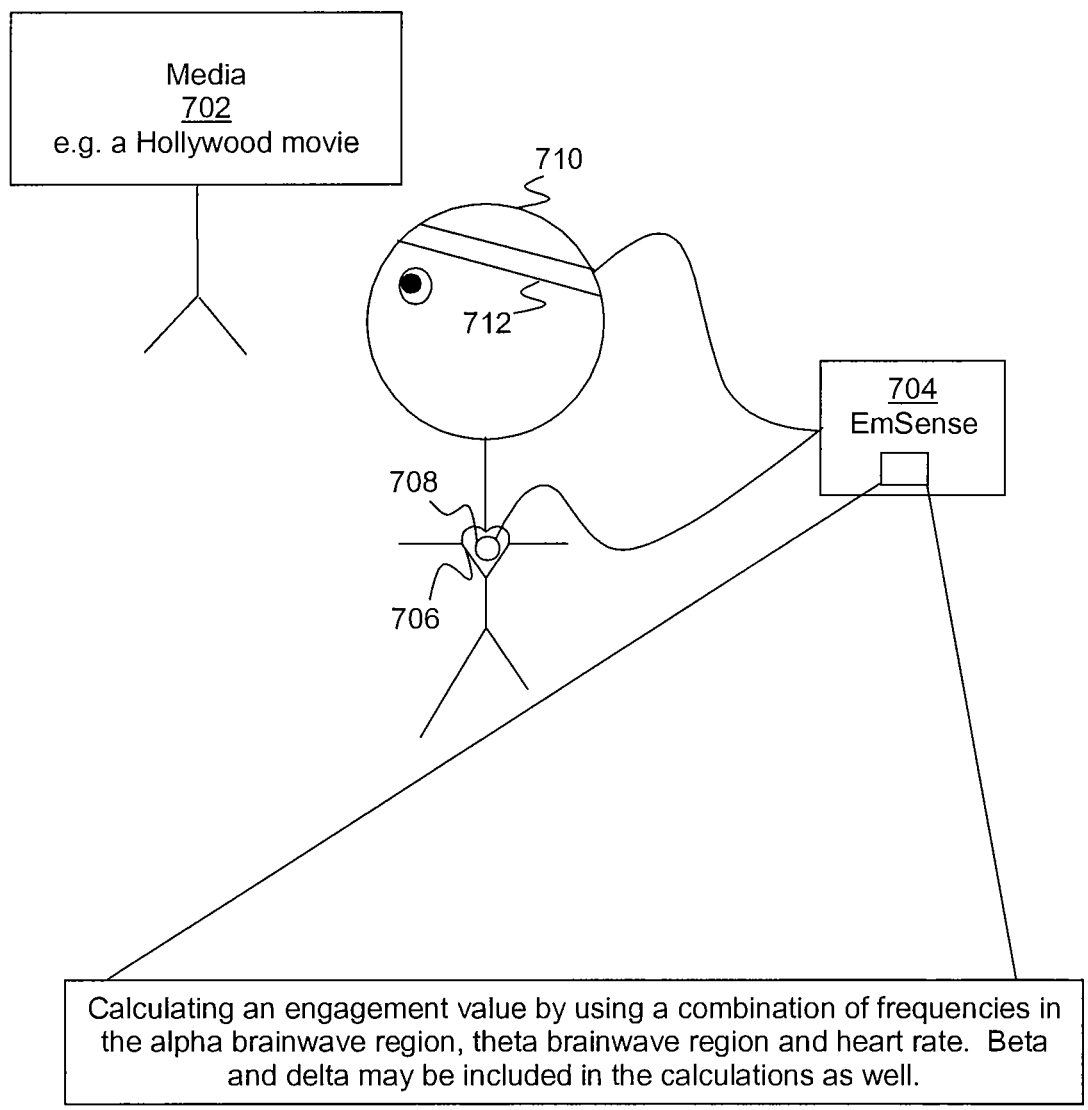
FIG. 7 depicts a diagram 700 of an example of stimulating an individual with a media while calculating an engagement value relating the individual's engagement with the media.

FIG. 7 depicts a diagram 700 of an example of stimulating an individual with a media while calculating an engagement value relating the individual's engagement with the media. Diagram 700 includes media 702, processing device 704, heart 706, electrode 708, individual 710, and headset 712. As depicted, individual 712 watches a Hollywood movie, media 702 while having his engagement level monitored by the processing device 704. Signals are collected from the head and the heart 706 via electrode 708 and headset 712. These signals are transmitted to processing device 704 for processing into an engagement value. Notably, delta, alpha, theta, and beta waves are all received by the headset 712, and are transmitted to the processing device 704 whether or not they are each actually used.

In some embodiments an aggregate of a number of individual engagement values derived from physiological responses is created determining a group response to a media. The aggregation can be by an average response for the number of individuals or by a higher ordered approximation.

Figure 8:
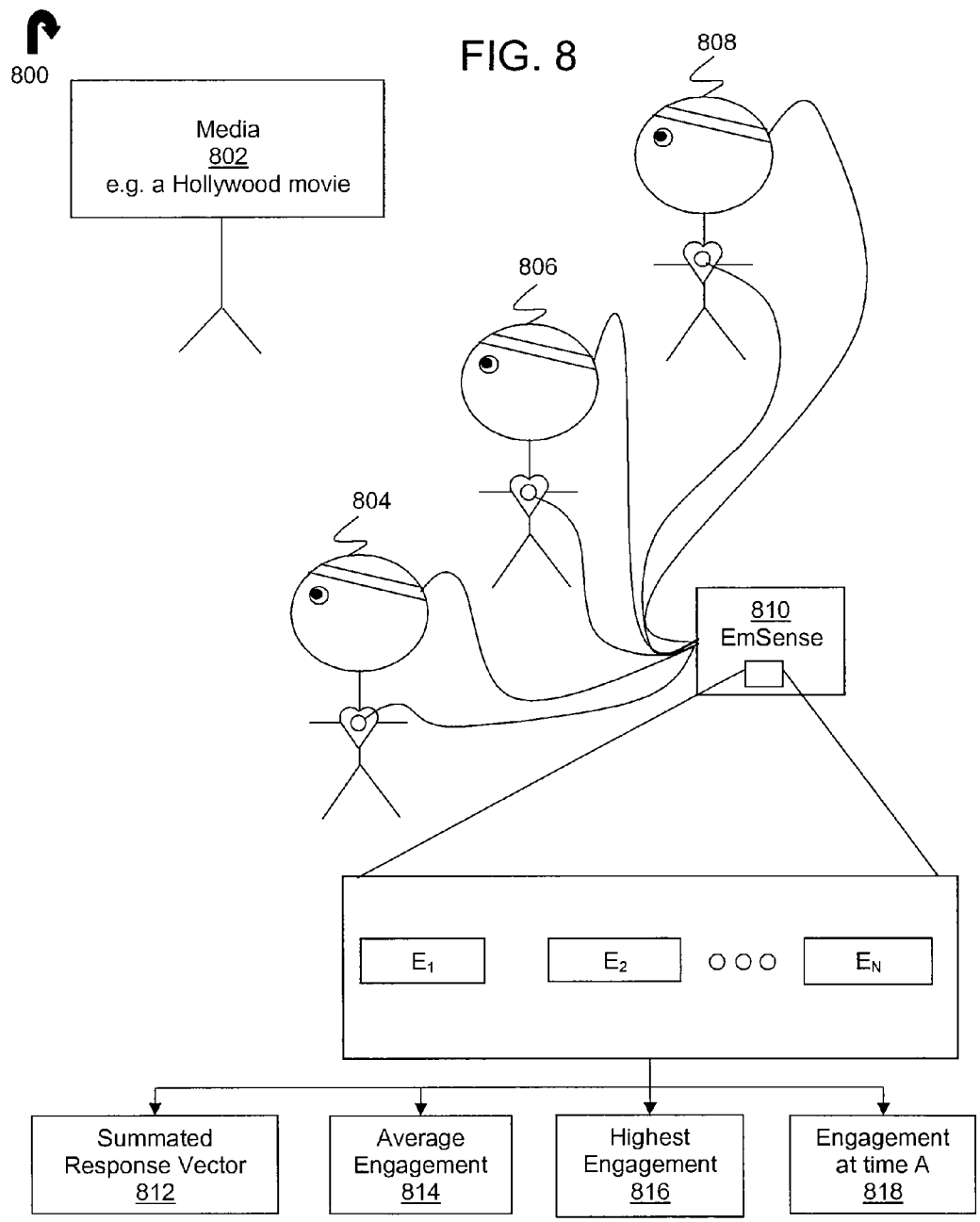
FIG. 8 depicts a diagram 800 of an example of stimulating a plurality of individuals with a media and calculating relevant values based on their engagement with the media.

FIG. 8 depicts a diagram 800 of an example of stimulating a plurality of individuals with a media and calculating relevant values based on their engagement with the media. Diagram 800 includes media 802, first individual 804, second individual 806, third individual 808, processing device 810, summated response vector 812, average engagement 814, highest engagement 816, and engagement at time 818. In the example of FIG. 8, individuals 804, 806, and 810 are engaged in a media, in this example they are watching a movie. The processing device 810 receives signals in accordance with the discussion of FIG. 1, and calculates engagements values. These engagement values are used to produce statistical information about the media based on the engagement values collected. E.g. summated response vector 812 may accept the engagement value of each of individuals 804, 806, and 810, and determine a number of individuals that responded to the media with engagement. In this example, a group response to the media may be obtained. Such additional statistical information as average engagement 814, highest engagement 816, and engagement at time 818 may be used to rank media based on a group response to media.

In some embodiments, an event is classified as a specific type of event by using a mathematical transform to compare the event with other events. Such mathematical transforms may include but are not limited to, an average, a first order derivative, a second order derivative, a polynomial approximation, a standard deviation from the mean, a standard deviation of derivatives from the mean, and profiles of the physiological responses, which can be implemented with convolution or other methods that takes into account one or more of: peaking in the middle, spiking in the beginning, being flat, etc.

FIG. 9 depicts diagrams 900 of graphs of examples of changes in engagement relative to events in time. Diagrams 900 include exciting engaging event 902, and unexciting disengaging event 904. In the example of FIG. 9, exciting engaging event 902 causes engagement to increase. The derivative of the engagement vector immediately following exciting engaging event 902 is clearly positive until the excitement has worn off resulting in a stable engagement. In the contrary, an excited engaged individual experiences unexciting disengaging event 904, which over the time immediately following, causes the engagement of the individual to decrease to the point where the individual is significantly less engaged than prior to the event.

Figure 10:
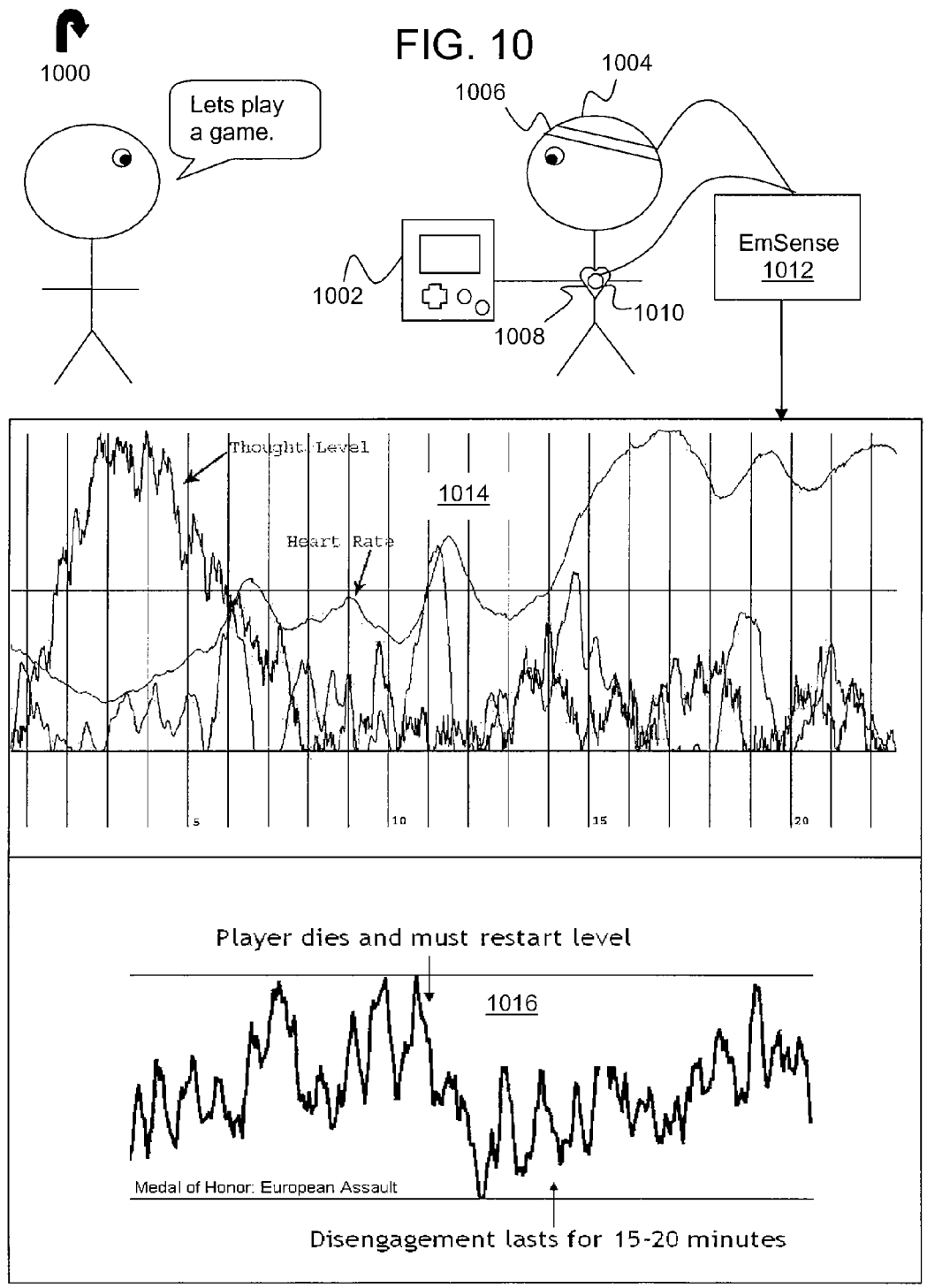
FIG. 10 depicts a diagram 1000 and data graphs of an example of stimulating an individual with a media, in this example a game, and recording the related levels of heart rate, thought, and engagement.

FIG. 10 depicts a diagram 1000 and data graphs of an example of stimulating an individual with a media, here a game, and recording the related levels of heart rate, thought, and engagement. Diagram 1000 includes game 1002, individual 1004, headset 1006, heart 1008, electrode 1010, processing device 1012, first graph 1014, and second graph 1016. First graph 1014 and second graph 1016 do not correspond to the same data from the same individual, but are from different experiments. In the example of FIG. 10, the individual 1004 plays a game while his brain waves are collected by headset 1006 and his heart signal is collected by processing device 1012. The resulting signal is analyzed in accordance with the discussion of FIG. 1, and the engagement is tracked. In graph 1014, the brainwaves and the heart rate are graphed. In the experiment an individual was observed and the graph was created. By comparing the actions of individual 1004 to graph 1014 over time, it was concluded that in periods of high intensity, when the individual identified that he had become engaged, his heart rate rose and his thought level, as identified by changes in alpha and theta, dropped. After finding that this engagement corresponded to the heart rate, and brain waves as discussed, graph 1016 was produced. Graph 1016 depicts the engagement of an individual with a game and a key point corresponding to disengagement is noted. This disengagement corresponds to that as described in the discussion of FIG. 9, although graph 1016 was produced through actual experiment.

In some embodiments, an integrated headset can be placed on a viewer's head for measurement of his/her physiological data while the viewer is watching an event of the media. The data can be recorded in a program on a computer that allows viewers to interact with media while wearing the headset.

FIG. 11 depicts a headset 1100 containing electrodes useful for collecting signals from a head of an individual. Headset 1100 includes processing unit 1101, three axis accelerometer 1102, silicon stabilization strip 1103, right EEG electrode 1104, heart rate sensor 1105, left EEG electrode 1106, battery module 1107, and adjustable strap 1108. FIG. 11 depicts an example of an integrated headset used with one embodiment of the present invention from different angles. Processing unit 1101 is a microprocessor that digitizes physiological data and can process the data into physiological responses that include but are not limited to thought, engagement, immersion, physical engagement, valence, vigor and others. A three axis accelerometer 1102 senses movement of the head. A silicon stabilization strip 1103 allows for more robust sensing through stabilization of the headset that minimizes movement. The right EEG electrode 1104 and left EEG electrode 1106 are prefrontal dry electrodes that do not need preparation to be used. Contact is needed between the electrodes and skin but without excessive pressure. The heart rate sensor 1105 is a robust blood volume pulse sensor positioned about the center of the forehead and a rechargeable or replaceable battery module 1107 is located over one of the ears. The adjustable strap 1108 in the rear is used to adjust the headset to a comfortable tension setting for many different head sizes.

In some embodiments, the integrated headset can be turned on with a push button and the viewer's physiological data is measured and recorded instantly. The data transmission can be handled wirelessly through a computer interface that the headset links to. No skin preparation or gels are needed on the viewer to obtain an accurate measurement, and the headset can be removed from the viewer easily and can be instantly used by another viewer. No degradation of the headset occurs during use and the headset can be reused thousands of times.

It will be appreciated to those skilled in the art that the preceding examples and embodiments are exemplary and not limiting to the scope of the present invention. It is intended that all permutations, enhancements, equivalents, and improvements thereto that are apparent to those skilled in the art upon a reading of the specification and a study of the drawings are included within the true spirit and scope of the present invention. It is therefore intended that the following appended claims include all such modifications, permutations, and equivalents as fall within the true spirit and scope of the present invention.

We claim:

1. A method for rating media, the method comprising:
   obtaining a first signal from a brain of an individual produced substantially while the individual is exposed to the media;
   obtaining a second signal from a heart of the individual produced substantially concurrently with the first signal from the brain;
   decomposing the first signal and the second signal into a frequency domain;
   calculating with a processor, an engagement value based on a first mathematical relationship between (1) a first frequency and (2) a second frequency from the frequency domain of the first signal and a second mathematical relationship between (1) a third frequency from the frequency domain of the second signal and (2) a result of the first mathematical relationship;
   comparing the engagement value with a reference value to determine a difference; and
   rating the media based on the difference between the engagement value and the reference value.

2. The method of claim 1, wherein at least one of the first frequency and the second frequency includes one or more of an alpha frequency or a theta frequency.

3. The method of claim 1, wherein the engagement value is associated with an event in the media.

4. The method of claim 1, wherein the second signal is sampled via a photoplethysmograph attached to a head of the individual.

5. The method of claim 1, wherein multiple engagement values from multiple individuals associated with an event in the media are aggregated to form an engagement response to the event.

6. The method of claim 1, wherein multiple engagement values from multiple individuals are included in a summated response vector identifying the number of persons that responded with engagement to the media.

7. The method of claim 1, wherein the decomposing is accomplished using a Fast Fourier transform or a wavelet analysis.

8. The method of claim 7, wherein the wavelet analysis is accomplished using a wavelet selected from a Mexican hat wavelet, a morlet wavelet, a daubechies wavelet, a beta wavelet, and a coiflet wavelet.

9. The method of claim 1, further comprising calculating a derivative of the engagement value representing a change in engagement over time.

10. The method of claim 2, wherein the engagement value is determined by calculating [heart rate/50]−[(theta−alpha)/(theta+alpha)].

11. The method of claim 1, wherein a length of each heart beat is monitored.

12. The method of claim 1 wherein the first signal includes an alpha frequency, a beta frequency, a delta frequency, a theta frequency and a total EEG power, the second signal includes a heart rate, and the engagement value is calculated by contrasting the heart rate with one or more of:
   $\theta-\alpha$,
   $\theta$,
   $\theta/\alpha$,
   $\Delta/\alpha$,
   $\beta/\alpha$, or
   total EEG power/$\alpha$.

13. The method of claim 1 wherein the first signal includes an alpha frequency, a beta frequency, a delta frequency, a theta frequency and a total EEG power, the second signal includes a heart beat, and the engagement value is calculated by contrasting a length of the heart beat with one or more of:
   $\alpha$,
   $\alpha/\theta$,
   $\alpha/\beta$,
   $\alpha/\Delta$,
   $\alpha$/total EEG power, or
   $(\alpha-\theta)/(\alpha+\theta)$.

14. The method of claim 1, wherein the media includes one or more of a television broadcast, a video game, an audiovisual advertisement, a board game, a card game, a live action event, a print advertisement or a web advertisement.

15. The method of claim 1, further comprising:
   identifying a point in time corresponding to the engagement value;
   identifying an event of the media occurring substantially concurrently with the point in time;
   correlating the engagement value with the event; and
   aligning the engagement value to the media.

16. A tangible machine readable storage medium comprising machine readable instructions which, when read, cause a machine to at least:
   decompose a first signal from a brain of an individual and a second signal from a heart of the individual into a frequency domain, the first and second signal produced substantially concurrently and while the individual is exposed to media;
   calculate an engagement value based on: (1) a first mathematical relationship between (a) a first frequency and (b) a second frequency from the frequency domain of the first signal and (2) a second mathematical relationship between (a) a third frequency from the frequency domain of the second signal and (b) a result of the first mathematical relationship;
   compare the engagement value with a reference value to determine a difference; and
   rate the media based on the difference between the engagement value and the reference value.

17. The medium of claim 16, wherein at least one of the first frequency and the second frequency includes one or more of an alpha frequency or a theta frequency.

18. The medium of claim 16, wherein the first signal includes an alpha frequency, a beta frequency, a delta frequency, a theta frequency and a total EEG power, the second signal includes a heart beat, and the engagement value is calculated by contrasting a length of the heart beat with one or more of:
   $\alpha$,
   $\alpha/\theta$,
   $\alpha/\beta$,
   $\alpha/\Delta$,
   $\alpha$/total EEG power, or
   $(\alpha-\theta)/(\alpha+\theta)$, wherein $\alpha$, $\beta$, $\Delta$, & $\theta$ are each found in the first signal.

19. The medium of claim 16, wherein the decomposing of the first signal and the second signal comprises using one or more of a fast Fourier transform or a wavelet analysis.

20. The medium of claim 16, wherein the media includes one or more of a television program, a video game, an audiovisual advertisement, a board game, a card game, a live action event, a print advertisement or a web advertisement.

21. The medium of claim 16, wherein the machine is further caused to:
align the signal relative to the media;
create a first aligned engagement value corresponding to a first event based on the alignment; and
compare the first aligned engagement value with a second aligned engagement value corresponding to a second event in time.

22. A system for rating media, the system comprising:
a data collector to obtain a first signal from a brain of an individual produced substantially while the individual is exposed to the media and a second signal from a heart of the individual produced substantially while the individual is exposed to the media; and
a processor to:
decompose the first signal and the second signal into a frequency domain;
calculate an engagement value based on a first mathematical relationship between (1) a first frequency and (2) a second frequency from the frequency domain of the first signal and a second mathematical relationship between (1) a third frequency from the frequency domain of the second signal and (2) a result of the first mathematical relationship;
compare the engagement value with a reference value to determine a difference; and
rate the media based on the difference between the engagement value and the reference.

23. The system of claim 22, wherein the data collector comprises one or more sensors included in an integrated sensor headset to measure a signal from the individual stimulated by the media.

24. The method of claim 1, wherein the reference value is determined by a developer of the media.

25. The method of claim 1, wherein the reference value is an average of a plurality of previously calculated engagement values for the media.

26. The method of claim 1, wherein the first mathematical relationship includes a ratio of (1) a first difference between the second frequency and the first frequency to (2) a sum of the first frequency and the second frequency.

27. The method of claim 26, wherein the second mathematical relationship includes a second difference between the third frequency and the result of the first mathematical relationship.

28. The method of claim 27, wherein the second mathematical relationship includes a percentage of the third frequency.

29. The method of claim 3, wherein the event is classified as a specific type of event using a mathematical transform to compare the event with one or more other events.

30. The method of claim 29, wherein the mathematical transform includes using an average.

31. The method of claim 29, wherein the mathematical transform includes a first order derivative.

32. The method of claim 29, wherein the mathematical transform includes a second order derivative.

33. The method of claim 29, wherein the mathematical transform includes a polynomial approximation.

34. The method of claim 29, wherein the mathematical transform includes a standard deviation from a mean.

35. The method of claim 29, wherein the mathematical transform includes a standard deviation of derivatives from a mean.

36. The method of claim 29, wherein the mathematical transform includes vectors and a positive derivative vector indicates an exciting type of event and a negative derivative vector indicates an unexciting type of event.

* * * * *

UNITED STATES PATENT AND TRADEMARK OFFICE
CERTIFICATE OF CORRECTION

PATENT NO. : 8,764,652 B2  
APPLICATION NO. : 11/845993  
DATED : July 1, 2014  
INVENTOR(S) : Hans C. Lee et al.

It is certified that error appears in the above-identified patent and that said Letters Patent is hereby corrected as shown below:

On the Title Page

In the Assignee (73): Replace "Nielson" with -- Nielsen --.

Signed and Sealed this
Twelfth Day of May, 2015

Michelle K. Lee
*Director of the United States Patent and Trademark Office*